(12) United States Patent
Borbas et al.

(10) Patent No.: US 8,530,459 B2
(45) Date of Patent: *Sep. 10, 2013

(54) SWALLOWTAIL MOTIFS FOR IMPARTING WATER SOLUBILITY TO PORPHYRINIC COMPOUNDS

(75) Inventors: K. Eszter Borbas, Stockholm (SE); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/316,009

(22) Filed: Dec. 9, 2011

(65) Prior Publication Data

US 2012/0082621 A1    Apr. 5, 2012

Related U.S. Application Data

(63) Continuation of application No. 12/064,656, filed as application No. PCT/US2006/041040 on Oct. 19, 2009, now Pat. No. 8,097,609.

(60) Provisional application No. 60/728,558, filed on Oct. 20, 2005.

(51) Int. Cl.
*C07B 47/00* (2006.01)
*C07D 487/22* (2006.01)
*A01N 43/36* (2006.01)

(52) U.S. Cl.
USPC .......................................... 514/185; 540/145

(58) Field of Classification Search
USPC .......................................... 540/145; 514/185
See application file for complete search history.

(56) References Cited

U.S. PATENT DOCUMENTS

| | | | |
|---|---|---|---|
| 6,212,093 B1 | 4/2001 | Lindsey | |
| 6,272,038 B1 | 8/2001 | Clausen et al. | |
| 6,596,935 B2 | 7/2003 | Lindsey et al. | |
| 6,916,982 B2 | 7/2005 | Loewe et al. | |
| 8,097,609 B2 * | 1/2012 | Borbas et al. | 514/185 |
| 2004/0044197 A1 | 3/2004 | Pandey et al. | |
| 2004/0110731 A1 | 6/2004 | Chan et al. | |
| 2004/0202612 A1 | 10/2004 | Adair | |
| 2005/0137180 A1 | 6/2005 | Robinson et al. | |
| 2005/0277770 A1 | 12/2005 | Balakumar et al. | |
| 2007/0108438 A1 | 5/2007 | Lindsey et al. | |

FOREIGN PATENT DOCUMENTS

| WO | WO 2007064841 A2 | 6/2007 |
|---|---|---|
| WO | WO 2007064842 A2 | 6/2007 |

OTHER PUBLICATIONS

International Search Report and Written Opinion, PCT/US06/41040, Sep. 21, 2007.
Borbas K E et al. Bioconjugatable porphyrins bearing a compact swallowtail motif for water solubility (2006), vol. 17, pp. 638-653.
Borbas K E et al. A compact water-soluble porphyrin bearing an iodoacetamido bioconjugatable site. Organic & Biomolecular Chemistry (2008), vol. 6, pp. 187-194.

* cited by examiner

*Primary Examiner* — Paul V. Ward
(74) *Attorney, Agent, or Firm* — Myers Bigel Sibley & Sajovec, P.A.

(57) ABSTRACT

Porphyrinic compounds that contain solubilizing groups are described, along with methods of making and using the same and compositions comprising such compounds. Examples of such compounds include compounds compounds of Formula I:

$$R^3-L-Z-(CH)_n\begin{matrix}Alk^1R^1\\ \\Alk^2R^2\end{matrix} \quad (I)$$

wherein: Z is a porphyrinic macrocycle, $Alk^1$ and $Alk^2$ are each independently an alkylidene chain; L is a linking group or is absent; $R^1$ is preferably an ionic group or polar group; $R^2$ is an ionic group, polar group, bioconjugatable group, or targeting group; $R^3$ is present or absent and when present is a halo group, bioconjugatable group, or targeting group, n is 0 or 1 (that is, the CH group is present, or $Alk^1$ and $Alk^2$ are bonded directly to a carbon of the porphyrinic macrocycle Z); or a salt thereof.

15 Claims, No Drawings

SWALLOWTAIL MOTIFS FOR IMPARTING WATER SOLUBILITY TO PORPHYRINIC COMPOUNDS

RELATED APPLICATIONS

This application is a continuation of U.S. patent application Ser. No. 12/064,656, filed Jul. 8, 2009 now U.S. Pat. No. 8,097,609, now allowed, which is a national phase application of PCT Application PCT/US2006/041040, filed Oct. 19, 2006, and published in English on Apr. 26, 2007, as International Publication No. WO 2007/047925, and which claims the benefit of U.S. Provisional Patent Application Ser. No. 60/728,558, filed Oct. 20, 2005, the disclosure of each of which is incorporated by reference herein in its entirety.

GOVERNMENT FUNDING

This invention was made with Government support under Grant No. GM36238 from the National Institutes of Health. The US Government has certain rights to this invention.

FIELD OF THE INVENTION

The present invention concerns substituted porphyrinic compounds and methods of making and using the same.

BACKGROUND OF THE INVENTION

A large and growing number of applications require porphyrinic macrocycles that are water-soluble and are suited for conjugation in a variety of formats. The applications encompass flow cytometry, cellular and whole-organism imaging, sensing, photodynamic therapy, biomimetic catalysis, and radical scavenging. The success of these applications relies on a host of factors, including (1) significant solubility in aqueous saline solutions, thereby avoiding intermolecular aggregation (and excited-state quenching), (2) minimal non-specific binding to cellular components, (3) incorporation of a single reactive group for conjugation, thereby avoiding crosslinking and mixtures of products, and (4) robust synthesis affording ample quantities for experimentation.

The large hydrophobic face of porphyrinic macrocycles presents a challenge to water-solubilization. Prior approaches to achieve water solubility of porphyrins have largely relied on uroporphyrin,[1] meso-tetrakis[4-(N-methyl)pyridinium] porphyrin,[2] and meso-tetrakis(4-sulfophenyl)porphyrin[2] (Chart 1).

Chart 1

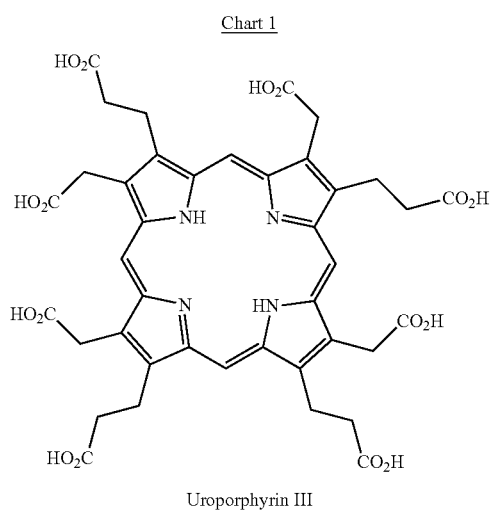

Uroporphyrin III

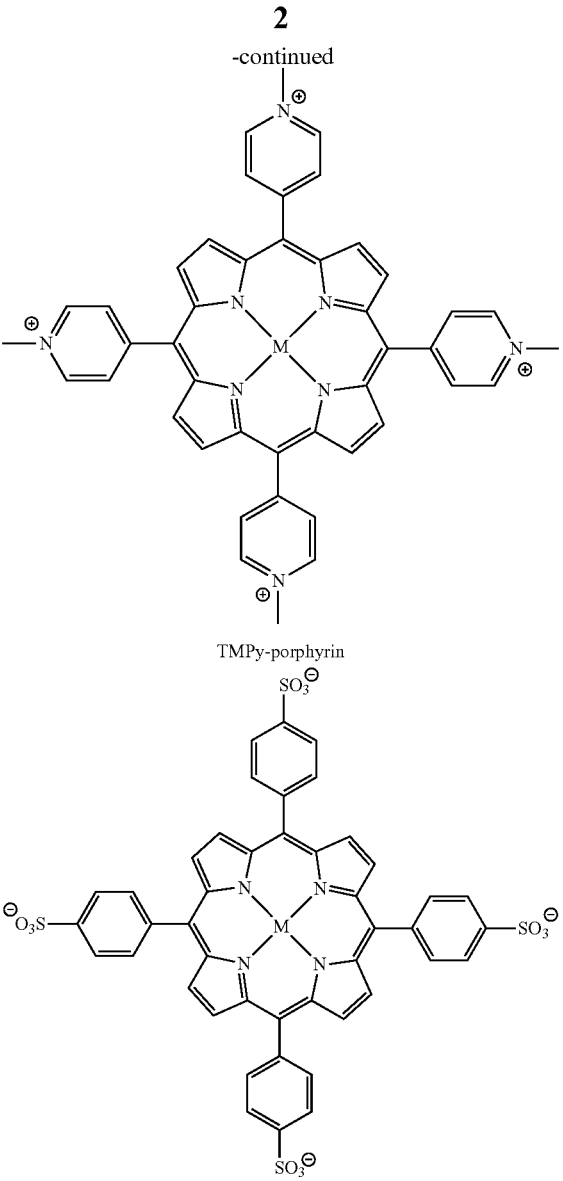

TMPy-porphyrin

Other approaches have entailed attachment of the following motifs to the porphyrin via a meso-aryl group: oligoethylene glycol (OEG) attached to a phenol,[3,4] multi-OEG dendrimers,[5] glycosyl units attached to phenols,[6] and alkyl polyamine[7] or polycarboxy chains.[8] While each group has merit, the porphyrins shown in Chart 1 are not suited for bioconjugation, and some of the other groups examined have mass>10-times that of porphyrin. With the exception of the very recent work of Sessler,[9] few new water-solubilizing motifs have been investigated for use with porphyrinic macrocycles.

In addition to water solubility, the presence of a bioconjugatable group is essential for attachment to substances ranging from nanoparticles to biological targeting agents. Indeed, porphyrinic molecules have been attached to diverse targeting agents including peptides,[10] estrogen,[11] acridine,[12] antibodies,[13] transferrin,[14] epidermal growth factor,[15] low density lipoprotein,[16] nucleic acids,[17] and polymers such as polylysine[18] or polyvinyl alcohol.[15] In each of these cases, the success of the bioconjugation places a premium on high solubility of the porphyrinic compound in aqueous media.

We recently found that branched-alkyl groups (e.g., tridec-7-yl) known as 'swallowtail' substituents are very effective in imparting a high level of organic solubility to porphyrins.[19]

The long hydrocarbon chains of the swallowtail motif project over both surfaces of the plane of the macrocycle, suppressing π-π interaction between the porphyrin rings.[19] Such hydrocarbon swallowtails were shown earlier to impart excellent solubility in organic media to perylene dyes, which otherwise are quite insoluble.[20] By contrast, the majority of prior water-solubilization motifs for use with porphyrins have relied on meso-aryl substituents that provide little facial encumbrance (Chart 1).

SUMMARY OF THE INVENTION

A first aspect of the present invention is a compound of Formula I or I':

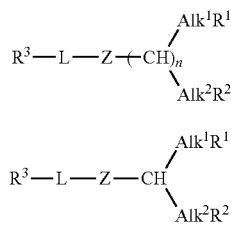

wherein:

$Alk^1$ and $Alk^2$ are each independently an alkylidene chain (e.g., a C1-C50 alkylidene chain);

Z is a porphyrinic macrocycle (e.g., a porphyrin, chlorin, bacteriochlorin, or isobacteriochlorin);

L is a linking group or is absent;

$R^1$ is an ionic group, polar group, bioconjugatable group, or targeting group (preferably an ionic group or polar group);

$R^2$ is an ionic group, polar group, bioconjugatable group, or targeting group;

$R^3$ is present or absent and when present is a halo group, bioconjugatable group, or targeting group, n is 0 or 1 (that is, the CH group is present, or $Alk^1$ and $Alk^2$ are bonded directly to a carbon of the porphyrinic macrocycle Z);

or a salt thereof.

A second aspect of the present invention is chlorins of Formula Va and bacteriochlorins of Formula Vb:

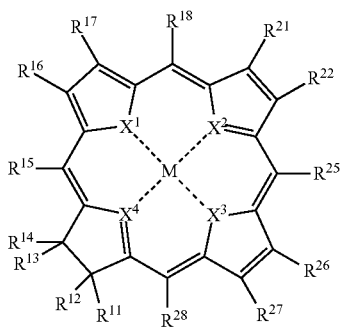

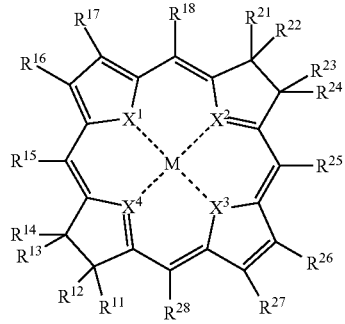

wherein:

M is a metal or is absent;

$X^1, X^2, X^3$ and $X^4$ are each independently selected from the group consisting of Se, NH, $CH_2$, O and S;

at least one pair (e.g., one, two, three or all four pairs) of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R' is an ionic group, polar group, bioconjugatable group, or targeting group;

$R^{11}, R^{12}, R^{15}, R^{16}, R^{17}, R^{18}, R^{21}, R^{22}, R^{23}, R^{24}, R^{25}, R^{26}, R^{27}$, and $R^{28}$ are as described above, or otherwise independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, acyloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxyacylamino, aminoacyloxy, linking groups, surface attachment groups, and groups of Formula II:

wherein $R^4$ and $R^5$ are each independently an ionic group or polar group, and $Alk^3$ and $Alk^4$ are each independently a C1-C50 alkylidene chain;

wherein each of $R^{11}$ and $R^{12}$, $R^{13}$ and $R^{14}$, $R^{21}$ and $R^{22}$, or $R^{23}$ and $R^{24}$ can together form =O;

and wherein each of $R^{11}$ and $R^{12}$, $R^{13}$ and $R^{14}$, $R^{21}$ and $R^{22}$, or $R^{23}$ and $R^{24}$, can together form spiroalkyl;

and at least one pair (e.g., one, two, three or all four pairs) of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R' is an ionic group, polar group, bioconjugatable group, or targeting group.

or a salt thereof.

Compounds of the present invention (sometimes referred to as "active compounds" herein) include compounds of Formula I (including Ia, Ib, and Ic as shown below), compounds of Formula Va and Vb, and pharmaceutically acceptable salts, prodrugs and conjugates thereof.

A further aspect of the invention is a method for treating a target in a subject in need thereof, comprising: (i) administering to the subject the active compound as described herein or a pharmaceutically acceptable conjugate thereof that preferentially associates with the target, and (ii) irradiating the target with light of a wavelength and intensity sufficient to treat the target. Suitable subjects include but are not limited to subjects afflicted with opportunistic infections, with burns (particularly burns that have become infected), sepsis, with ulcers, periodontal disease, atherosclerosis, cosmetic and dermatologic conditions, acne, infectious diseases, tissues that require sealing such as in wounds or surgical incisions, and subjects afflicted with neoplastic disease or cancer.

A further aspect of the invention is a photodynamic therapy method for treating hyperproliferative tissue in a subject in need thereof, comprising: (i) administering to the subject an active compound as described herein or a pharmaceutically acceptable conjugate thereof that preferentially associates with the hyperproliferative tissue, and (ii) irradiating the target with light of a wavelength and intensity sufficient to activate the compound, and thereby treat the hyperproliferative tissue.

A further aspect of the invention is a method for detecting the presence of a target such as hyperproliferative tissue in a subject, comprising: (i) administering to the subject an active compound as described herein or a pharmaceutically acceptable conjugate thereof that preferentially associates with the target; and then (ii) visualizing the compound within the patient.

A further aspect of the present invention is a kit to treat hyperproliferative disorders, comprising the active compound described herein or a pharmaceutically acceptable conjugate thereof and instructions teaching a method of photodynamic therapy.

A further aspect of the present invention is a kit to label specific tissues for diagnosis comprising the active compound described herein or a pharmaceutically acceptable conjugate thereof and instructions teaching a method of imaging (e.g., magnetic resonance imaging).

A further aspect of the present invention is, in a method of detecting particles such as cells by flow cytometry, where the particles are labelled with a detectable luminescent compound, the improvement comprising utilizing a bacteriochlorin as described herein as the luminescent compound.

The foregoing and other objects and aspects of the invention are explained in greater detail in the specification set forth below.

DETAILED DESCRIPTION OF THE PREFERRED EMBODIMENTS

The disclosures of all United States patent references cited herein are to be incorporated by reference herein as if fully set forth.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhekyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocylooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a' straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include at least one 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as H, alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocyclo amino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

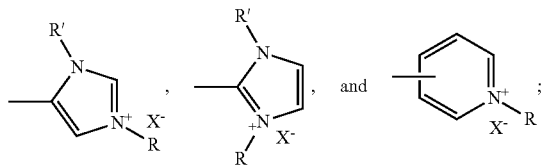

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O), heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

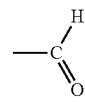

"Acetal" as used herein refers to a group of the formula:

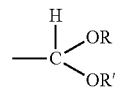

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and NH$_4$Cl.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula LnX$_3$ where Ln is a lanthanide and X is halo such as Cl, Br, I, etc., triflate or OTf, etc., and with examples specific examples including but not limited to: Yb(OTf)$_3$, InCl$_3$, Sc(OTf)$_3$, MgBr$_2$ and CeCl$_3$.

"Porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g phthalocyanines, porphyrazines, naphthalocyanines, subphthalocyanines, and porphyrin isomers).

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Crown ether" as used herein means a macrocyclic polyether whose structure exhibits a conformation with a so-called hole capable of trapping cations by coordination with a lone pair of electrons on the oxygen atoms (see generally McGraw-Hill Dictionary of Scientific and Technical Terms (3d ed. 1984)). Crown ethers are a species of macrocyclic ligand. The crown ether may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates)

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis*, 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or —C(O)CH$_3$), benzoyl (Bn or —C(O)C$_6$H$_5$), and trimethylsilyl (TMS or —Si(CH$_3$)$_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, *rickettsia*, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia), Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions.

"Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizes to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

Subjects to be treated by the methods of the present invention for diagnostic or therapeutic purposes include both human subjects and animal subjects (particularly mammalian subjects such as dogs, cats, horses, monkeys, chimpanzees, etc.) for veterinary purposes.

1. Compounds and Methods of Making.

As noted above, active compounds of the invention include compounds of Formula I or I':

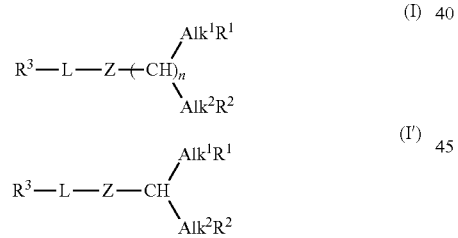

wherein:

Alk$^1$ and Alk$^2$ are each independently a C1-C50 alkylidene chain;

Z is a porphyrinic macrocycle;

L is a linking group or is absent;

R$^1$ is an ionic group or polar group;

R$^2$ is an ionic group, polar group, bioconjugatable group, or targeting group;

R$^3$ is present or absent and when present is a halo group, bioconjugatable group, or targeting group, n is 0 or 1 (that is, the CH group is present, or Alk$^1$ and Alk$^2$ are bonded directly to a carbon of the porphyrinic macrocycle Z, see, e.g., Formula Va-b below); or a salt thereof.

Specific examples of the foregoing include, but are not limited to:

(a) porphyrins of Formula Ia:

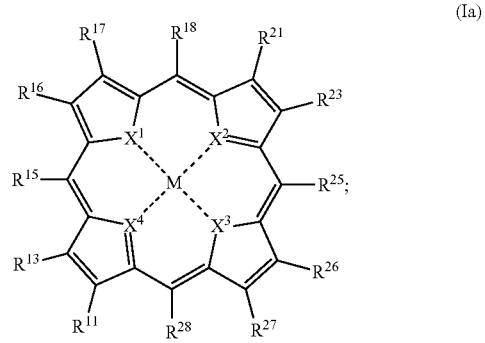

(b) chlorins of Formula Ib:

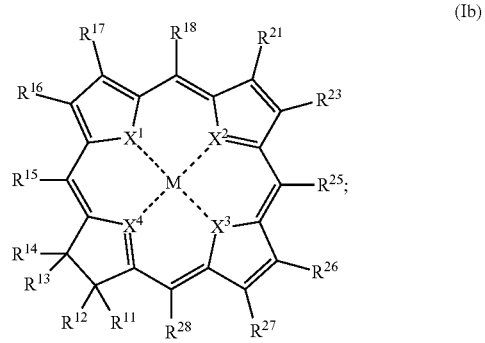

(c) bacteriochlorins of Formula Ic:

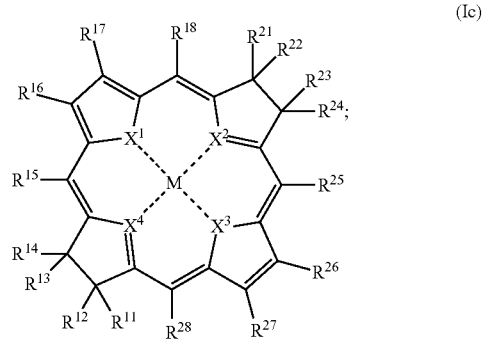

wherein:

M is a metal or is absent;

X$^1$, X$^2$, X$^3$ and X$^4$ are each independently selected from the group consisting of Se, NH, CH$_2$, O and S;

R$^{11}$, R$^{12}$, R$^{13}$, R$^{14}$, R$^{15}$, R$^{16}$, R$^{17}$, R$^{18}$, R$^{21}$, R$^{22}$, R$^{23}$, R$^{24}$, R$^{25}$, R$^{26}$, R$^{27}$, and R$^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and groups of Formula II:

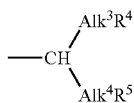
(II)

wherein $R^4$ and $R^5$ are each independently an ionic group or polar group, and $Alk^3$ and $Alk^4$ are each independently a C1-C50 alkylidene chain;

wherein each of $R^{11}$ and $R^{12}$, $R^{13}$ and $R^{14}$, $R^{21}$ and $R^{22}$, or $R^{23}$ and $R^{24}$ can together for m=O;

and wherein each of $R^{11}$ and $R^{12}$, $R^{13}$ and $R^{14}$, $R^{21}$ and $R^{22}$, or $R^{23}$ and $R^{24}$, can together form spiroalkyl;

subject to the proviso that at least one of $R^{11}$, $R^{12}$, $R^{13}$, $R^{14}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ is a bond to L and at least one thereof is a bond to said CH group of Formula I;

and salts thereof.

In the case of bacteriochlorins of Formula Ic and V, $X^2$ and $X^4$ are preferably both N.

In the case of bacteriochlorins of Formula Ic, at least one pair of $R^{13}$ and $R^{14}$, and $R^{23}$ and $R^{24}$, are not both H.

In some embodiments of the foregoing, one of $R^{15}$, $R^{18}$, $R^{25}$ and $R^{28}$ is a bond to said CH group of Formula I. In preferred embodiments such compounds are porphyrins of formula Ia or chlorins of formula Ib.

In some embodiments of the foregoing:
$R^{15}$ is a bond to L and $R^{25}$ is a bond to said CH group of Formula I;
$R^{25}$ is a bond to L and $R^{15}$ is a bond to said CH group of Formula I;
$R^{18}$ is a bond to L and $R^{28}$ is a bond to said CH group of Formula I; or
$R^{28}$ is a bond to L and $R^{18}$ is a bond to said CH group of Formula I.

In preferred embodiments such compounds are porphyrins of formula Ia or chlorins of formula Ib.

In some embodiments of the foregoing:
$R^{15}$ is a bond to L and $R^{18}$ is a bond to said CH group of Formula I;
$R^{18}$ is a bond to L and $R^{25}$ is a bond to said CH group of Formula I;
$R^{25}$ is a bond to L and $R^{28}$ is a bond to said CH group of Formula I; or
$R^{28}$ is a bond to L and $R^{15}$ is a bond to said CH group of Formula I.

In preferred embodiments such compounds are porphyrins of formula Ia or chlorins of formula Ib.

In some embodiments of the foregoing, one of $R^{11}$, $R^{12}$, $R^{13}$, $R^{14}$, $R^{16}$, $R^{17}$, $R^{21}$, $R^{22}$, $R^{23}$, $R^{24}$, $R^{26}$, or $R^{27}$ is a bond to said CH group of Formula I. In preferred embodiments such compounds are bacteriochlorins of Formula Ic.

In some embodiments of the foregoing, one of $R^{11}$, $R^{12}$, $R^{13}$, $R^{14}$, $R^{16}$, or $R^{17}$ is a bond to L, and one of $R^{21}$, $R^{22}$, $R^{23}$, $R^{24}$, $R^{26}$, or $R^{27}$ is a bond to said CH group of Formula I. In preferred embodiments such compounds are bacteriochlorins of formula Ic.

In some embodiments of the foregoing, one of $R^{16}$, $R^{17}$, $R^{26}$, or $R^{27}$ is a bond to said CH group of Formula I. In preferred embodiments such compounds are bacteriochlorins of formula Ic.

In some embodiments of the foregoing:
$R^{16}$ is a bond to L and $R^{26}$ is a bond to said CH group of Formula I;

$R^{26}$ is a bond to L and $R^{16}$ is a bond to said CH group of Formula I;
$R^{17}$ is a bond to L and $R^{27}$ is a bond to said CH group of Formula I; or
$R^{27}$ is a bond to L and $R^{17}$ is a bond to said CH group of Formula I.

In preferred embodiments such compounds are bacteriochlorins of formula Ic.

Another aspect of the present invention is chlorins of Formula Va and bacteriochlorins of Formula Vb:

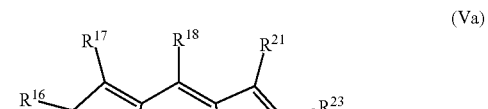
(Va)

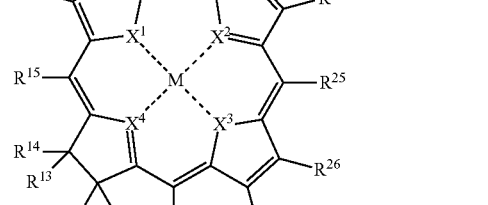
(Vb)

wherein:
M is a metal or is absent;
$X^1$, $X^2$, $X^3$ and $X^4$ are each independently selected from the group consisting of Se, NH, $CH_2$, O and S;
$R^{11}$, $R^{12}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, and groups of Formula

(II)

wherein $R^4$ and $R^5$ are each independently an ionic group or polar group, and $Alk^3$ and $Alk^4$ are each independently a C1-C50 alkylidene chain;

wherein each of $R^{11}$ and $R^{12}$, $R^{13}$ and $R^{14}$, $R^{21}$ and $R^{22}$, or $R^{23}$ and $R^{24}$ can together form=O;

and wherein each of $R^{11}$ and $R^{12}$, $R^{13}$ and $R^{14}$, $R^{21}$ and $R^{22}$, or $R^{23}$ and $R^{24}$, can together form spiroalkyl; and at least one pair (e.g., one, two, three or all four pairs) of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C1-C50 alkylidene chain, and R' is an ionic group, polar group, bioconjugatable group, or targeting group.

or a salt thereof.

For example, in some embodiments, $R^{11}$ or $R^{13}$ is $Alk^1R^1$ wherein $Alk^1$ is a C1-C50 alkylidene chain, and $R^1$ is an ionic group, polar group, bioconjugatable group, or targeting group; and $R^{12}$ or $R^{14}$ is $Alk^2R^2$ wherein $Alk^2$ is a C1-C50 alkylidene chain, and $R^2$ is an ionic group, polar group, bioconjugatable group, or targeting group; subject to the proviso that $R^{12}$ is $Alk^2R^2$ when $R^{11}$ is $Alk^1R^1$ and subject to the proviso that $R^{14}$ is $Alk^2R^2$ when $R^{13}$ is $Alk^1R^1$.

For example, in some embodiments, $R^{21}$ or $R^{23}$ is $Alk^{41}R^{41}$ wherein $Alk^{41}$ is an alkylidene chain, and $R^{41}$ is an ionic group, polar group, bioconjugatable group, or targeting group; and/or $R^{22}$ or $R^{24}$ is $Alk^{42}R^{42}$ wherein $Alk^{42}$ is an alkylidene chain, and $R^{42}$ is an ionic group, polar group, bioconjugatable group or targeting group; subject to the proviso that $R^{22}$ is $Alk^{42}R^{42}$ when $R^{21}$ is $Alk^{41}R^{41}$ and subject to the proviso that $R^{24}$ is $Alk^{42}R^{42}$ when $R^{23}$ is $Alk^{41}R^{41}$);

In some embodiments, when the compound is a bacteriochlorin of Formula Vb, $R^{23}$ and $R^{24}$ are preferably not both H.

In some embodiments, $R^1$ is an ionic group or polar group, and $R^2$ is a bioconjugatable group or targeting group.

In some embodiments, $R^1$ and $R^2$ are both independently selected ionic groups or polar groups, and one, or both, of $R^{41}$ and $R^{42}$ are independently selected bioconjugatable or targeting groups.

Compounds of Formulas I (including Ia, Ib, and Ic) and Formula V can be made by the methods described herein or variations thereof that will be apparent to persons skilled in the art based upon the present disclosure.

Porphyrins and Chlorins. Compounds of Formula I, particularly porphyrins of Formula Ia and chlorins of Formula Ib, can be produced by reacting a dipyrromethane of Formula IV with a suitable aldehyde, or dipyrromethane-dicarbinol, in accordance with known techniques.

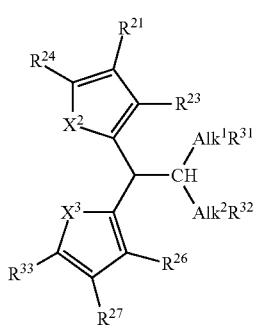

(IV)

wherein:

$R^{31}$ and $R^{32}$ are each independently halo, —$XR^{35}$ where X is O, S, COO or NH and $R^{35}$ is H or a protecting group; or an ionic group, polar group, bioconjugatable group, or targeting group (in protected or unprotected form);

$R^{21}$, $R^{23}$, and $R^{27}$ are as given above; and $R^{33}$ and $R^{34}$ are H, aldehyde, or N,N-dialkylaminomethyl. Once the core ring is formed, the protecting groups (and optionally the oxygen covalently bonded thereto) can be removed and replaced with suitable polar, ionic, bioconjugatable or targeting groups in accordance with known techniques.

Compounds of Formula IV are produced by reacting an aldehyde or acetal of Formula III

(III)

wherein $R^{31}$ and $R^{32}$ are as given above (e.g., in protected form) and $R^{36}$ is an aldehyde or acetal, with pyrrole (e.g., at least one pyrrole, each of which may be substituted or unsubstituted, and which together are preferably provided in excess) in a (preferably non-aqueous) reaction system (or "mixture") in the presence of a catalyst to form a dipyrromethane, quenching the reaction system by adding a base, separating the catalyst from the reaction system (e.g., by gravity or filtration) and then separating the pyrrole from the non-aqueous reaction system to produce a dipyrromethane of Formula IV as an intermediate. The one or more pyrroles may be unsubstituted or substituted 1, 2, 3 or 4 times with independently selected substituents of the same type as set forth in connection with $R^{21}$ and $R^{23}$, and $R^{26}$ and $R^{27}$, above. The reaction can be carried out in analogous manner to that described in J. Lindsey, S. Dhanalekshmi, J. Laha, and M. Taniguchi, *Scalable Synthesis of Dipyrromethanes*, US Patent Application No. 20050038262.

The amount of the compound of Formula III in the reaction system will vary depending upon the particular aldehyde or acetal used, but in general the molar ratio of the pyrrole to the compound of Formula III is 250:1 to 5,000:1. Stated differently, in general the amount of compound of Formula III is from 0.05 or 0.5 to 1 or 5 percent by weight of the system, or more, and the amount of pyrrole in the system is generally from 95 or 98 to 99 or 99.9 percent by weight of the system, or more. The catalyst may be a Bronsted acid or a Lewis acid, and the amount of catalyst in the system is, in general, from 0.01 or 0.1 to 0.5 or 1 percent by weight of the system, or more. Stated otherwise, the molar amount of acid is generally about 0.01 to 100 times the molar amount of aldehyde or acetal in the system. Preferably the system contains not more than 5 or 10 percent by weight water as noted above, and more preferably the system is non-aqueous. The next step of the method involves (b) reacting the compound of Formula III with the pyrrole in the reaction system to form the dipyrromethane therein. The reaction temperature is not critical, but in general may be from −20 or 0 to 100° C., or more, and is preferably room temperature. The pressure of the system during the reaction is not critical, but is conveniently ambient pressure. The reaction may be carried out for any suitable time, typically up to 24 hours, and preferably up to one hour. After the reaction step, the method involves (c) quenching the reaction system by adding a base thereto. The base is preferably added without simultaneously adding an organic solvent or water to the reaction system, and in a preferred embodiment the reaction system hence remains non-aqueous during quenching. In general, at least 1 equivalent of base per acid catalyst, up to 10 equivalents of base per acid catalyst, is added. The base may conveniently be added as a pure or neat substance (which may be a liquid or dry powder), a slurry in pyrrole, etc. The method then involves (d) separating the catalyst from the (preferably non-aqueous) reaction system, preferably by a filtration technique (such as suction filtration or pressure filtration) or a gravity technique (such as centrifugation or settling, e.g., with subsequent decanting); and then (e) separating the pyrrole from the (preferably non-aqueous) reaction system to produce the compound of Formula IV a residual (e.g., by pumping off or evaporating the pyrrole).

Chlorins and Bacteriochlorins. Compounds of Formula Ic, Va and Vb can be made by self-condensing a compound, condensing a pair of compounds, or condensing a compound of Formula XII as a Western half with an appropriate Eastern half:

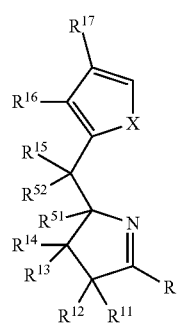

(XII)

in an organic solvent in the presence of an acid to produce the compound of Formula Ic or V, wherein:

R is an aldehyde or acetal group (for bacteriochlorins) or methyl (for chlorins);

X and $R^{11}$ to $R^{17}$ are as given above; and $R^{51}$ and $R^{52}$ are each H; or $R^{51}$ and $R^{52}$ together form a covalent bond.

Optionally, $R^{18}$ and $R^{28}$ in Formulas Ic and Va, Vb (H by this synthesis) is further substituted to replace H with additional substituents as described above in accordance with known techniques.

Bacteriochlorin compounds of Formula I are made from compounds of Formula XII when R is acetal by treating the compounds with an acid in an organic solvent. The acid is not critical, with examples including but not limited to $BF_3$ etherate, $SnCl_4$, $InCl_3$, trifluoroacetic acid, and toluenesulfonic acid. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air. When $R^{51}$ and $R^{52}$ are both H the reaction mixture preferably includes an oxidizing agent such as air or DDQ.

Compounds of Formulas XII are made from compounds of Formula XIII:

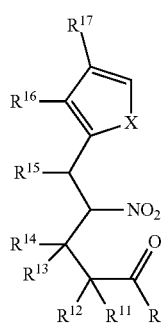

(XIII)

$R^{11}$ through $R^{17}$ are the same as given above in connection with Formula I, and R is acetal. In general, compounds of Formula XII are produced by deprotonating a compound of Formula XIII (e.g., by treating with anhydrous sodium methoxide) to produce a nitronate anion intermediate, and then cyclizing the intermediate with a deoxygenating agent (e.g., by combining the intermediate with an aqueous buffered $TiCl_3$ solution) to produce the compound of Formula IIa. Reaction conditions are not critical and numerous variations will be apparent to those skilled in the art. In general, compounds of Formula IIb are produced by treating a compound of Formula III with a metal (e.g., zinc and acetic acid in ethanol) to produce an N-oxide intermediate, and then cyclizing the intermediate with a deoxygenating agent (eg., Ti(0), Zn, NaOH/methanol; Zn, aqueous $NH_4Cl$/THF; $FeSO_4$, aqueous $NH_4Cl/CH_3CN$; Mg or Fe, $AcONH_4$/methanol; $Ph_3P$/toluene; S/toluene; $NaN_3$/toluene; Zn, NaI, $Me_3SiCl$/$CH_3CN$; etc.) to produce the compound of Formula III). Again reaction conditions are not critical and numerous variations will be apparent to those skilled in the art.

Compounds of Formula Ic or Va, Vb are made from compounds of Formula XII, where R is an aldehyde, by treating the compounds of Formula XII with an acid in an organic solvent in like manner as described above. Compounds of Formula XII where R is an aldehyde are made by oxidizing a corresponding compound of Formula XV:

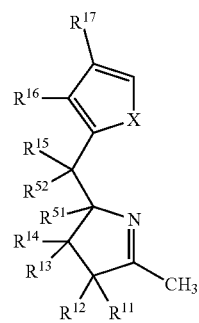

(XV)

in an organic solvent in the presence of an oxidizing agent to produce the compound of Formula XII. Any suitable solvent can be used, particularly ethereal solvents such as 1,4-dioxane, tetrahydrofuran, diethyl ether and dimethoxyethane. The reaction conditions are not critical and the reaction may be carried out at any suitable temperature, for example 0 to 100° C., preferably room temperature, for any suitable time, typically one to two hours. $SeO_2$ is currently preferred as the oxidizing agent, but any suitable oxidizing agent may be used. In general, when relatively powerful oxidizing agents are employed with alkyl groups that are activated by the presence of a π bond (allylic), the alkyl group can be oxidized to the aldehyde or ketone. The most common reagents for these transformations are selenium dioxide ($SeO_2$), chromium trioxide ($CrO_3$), chromyl chloride ($CrO_2Cl_2$), and $Pb(OAc)_4$. In addition, t-BuOOH/CuI oxidizes the allylic carbon of alkenyl conjugated ketones (Organic Synthesis, $2^{nd}$ Ed; Smith, M. B.; McGraw-Hill Higher Education: 2002; 272-279) and can also be used as oxidizing agents herein. A variety of chromium reagents have been used for allylic oxidations ((a) Dauben, W. G.; Lorber, M.; Fullerton, D. S. *J. Org. Chem.* 1969, 34, 3587-3592. (b) Fullerton, D. S.; Chen, C. M. *Synth. Commun.* 1976, 6, 217-220. (c) Salmond, W. G.; Barta, M. A.; Havens, J. L. *J. Org. Chem.* 1978, 43, 2057-

2059. (d) Parish, E. J.; Chitrakorn, S.; Wei, T.-Y. *Synth. Commun.* 1986, 16, 1371-1375. (e) Parish, E. J.; Wei, T.-Y. *Synth. Commun.* 1987, 17, 1227-1233. (f) Marshall, C. W.; Ray, R. E.; Laos, I.; Riegel, B. *J. Am. Chem. Soc.* 1975, 79, 6308-6313. (g) Amann, A.; Ourisson, G.; Luu, B. *Synthesis* 1987, 1002-1005. (h) Bora, U.; Chaudhuri, M. K.; Dey, D.; Kalita, D.; Kharmawphlang, W.; Mandal, G. C. *Tetrahedron* 2001, 57, 2445-2448) and can also be used as oxidizing agents herein. Examples include $CrO_3$-pyridine complex, $CrO_3$ and 3,5-dimethylpyrazole, pyridinium chlorochromate (PCC), pyridinium dichromate (PDC), sodium chromate, sodium dichromate in acetic acid, pyridinium fluorochromate, and 3,5-dimethylpyrazolium fluorochromate (VI). The 5-methyl group of a pyrrole-2-ester was oxidized by ceric ammonium nitrate ((a) Huggins, M. T.; Lightner, D. A. *Tetrahedron* 2000, 56, 1797-1810. (b) Tipton, A. K.; Lightner, D. A.; McDonagh, A. F. *J. Org. Chem.* 2001, 66, 1832-1838) and this can also be used as an oxidizing agent herein.

Compounds of Formula Ic and Va, Vb may be produced wherein $R^{18}$ and $R^{28}$ are H by the methods described above, and then $R^{18}$ or $R^{28}$ brominated in accordance with known techniques and further substituents added at position $R^{18}$ and $R^{28}$ in accordance with known techniques. Likewise other substituents can be added at positions $R^{11}$ through $R^{17}$ (or $R^{21}$ through $R^{27}$) by substitution (e.g., by bromination or formylation) in accordance with known techniques.

Chlorins and bacteriochlorins bearing polar/ionic-terminated dialkyl groups also can be prepared by reaction of compounds of Formula XII where $R^{13}$ and $R^{14}$ constitute the polar/ionic terminated dimethyl groups. In this regard, it should be noted that substituents other than geminal dialkyl in the pyrroline ring have been introduced in chlorin chemistry (see the spiroalkyl-chlorins in Taniguchi, M., et al., *J. Org. Chem.* 2002, 67, 7329-7342). A similar route is suitable for introduction of polar/ionic-terminated groups at the $R^{13}$ and $R^{14}$ positions.

The synthesis of the requisite precursor of Formula XII is shown in the synthetic scheme below. The starting compound 2-(2-nitroethyl)pyrrole undergoes Michael addition with an α,β-unsaturated ketone (XVI), where $R^x$ and $R^y$ constitute the alkylidene chains terminated with polar or ionic or bioconjugatable or targeting groups, which may be in protected form. Compounds of formula XVI are available by a variety of routes, including Wittig condensation of dimethyl (2-oxopropyl)phosphonate and the ketone $R^xC(O)R^y$. The product of the Michael addition is the nitro-hexanone pyrrole (XIII). For the preparation of chlorins via a tetrahydrodipyrrin, compound XIII undergoes reductive cyclization to give the N-oxide (XV-oxide), which upon deoxygenation affords the desired 1-methyl-2,3,4,5-tetrahydrodipyrrin XV. Compound XV serves as the Western half in chlorin syntheses. For the preparation of chlorins via a dihydrodipyrrin, compound XIII undergoes reductive cyclization to give desired 1-methyl-2,3-dihydrodipyrrin compound XV. Compound XV serves as the Western half in chlorin syntheses.

For the preparation of bacteriochlorins via a dihydrodipyrrin, compound XIII undergoes reductive cyclization to give compound XV; where R=acetal, XV undergoes self-condensation to afford the corresponding bacteriochlorin. Alternatively, where R=methyl, XV can be treated to conditions for oxidation of the terminal methyl group, affording dihydrodipyrrin-aldehyde XII. Compound XII also undergoes self-condensation to give the corresponding bacteriochlorin.

Examples of the foregoing may be carried out as shown in the Synthetic Scheme below.

Synthetic Scheme

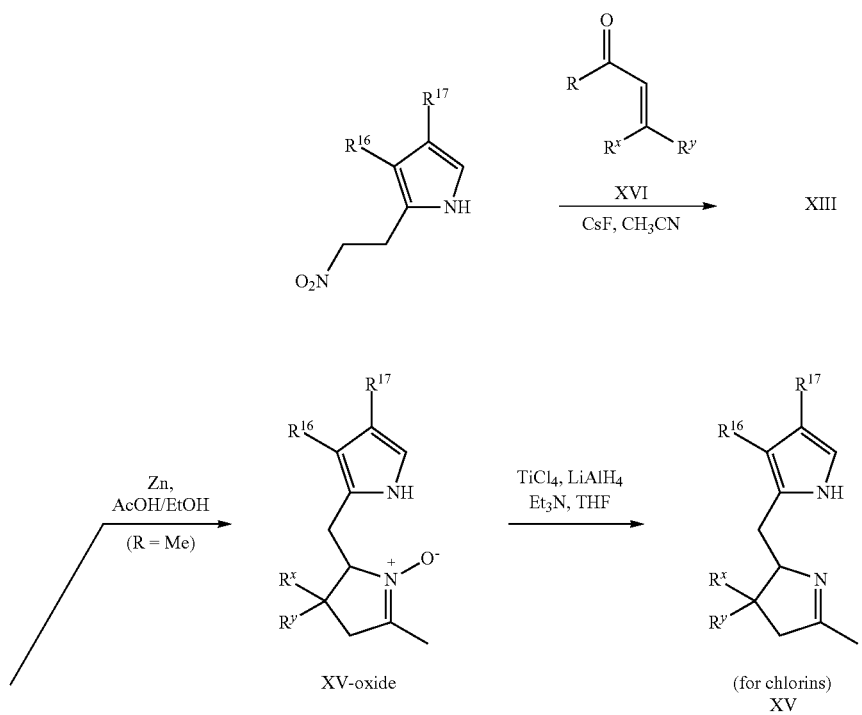

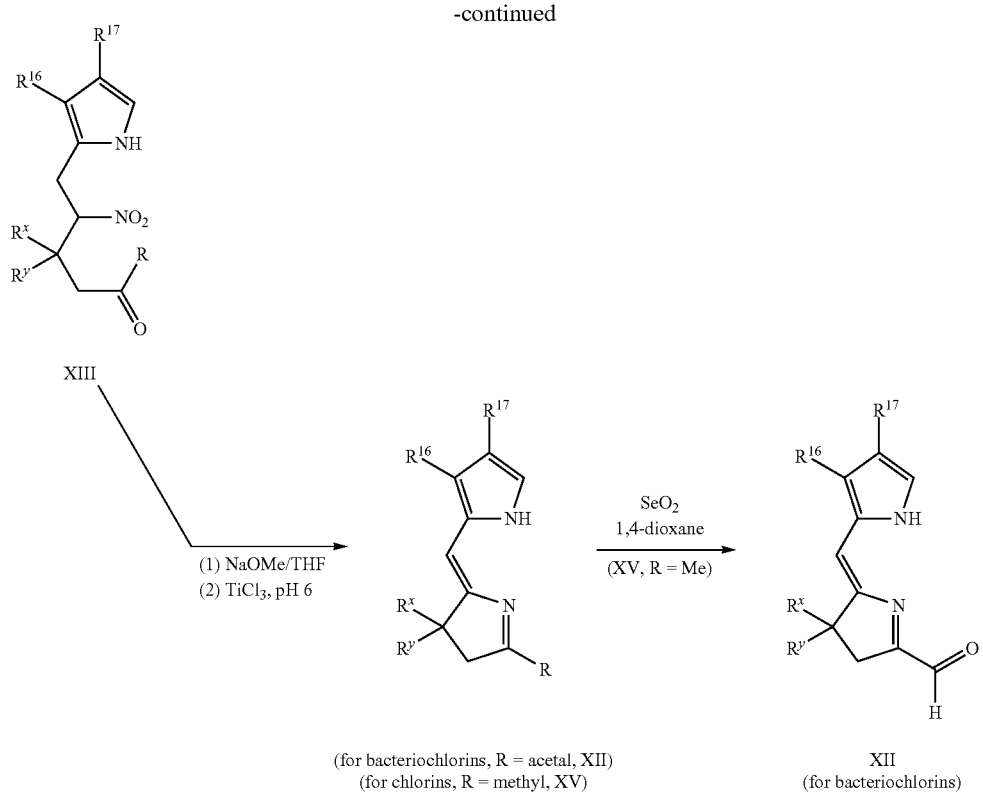

(for bacteriochlorins, R = acetal, XII)
(for chlorins, R = methyl, XV)

XII
(for bacteriochlorins)

A dipyrromethane of Formula IV can be converted to an Eastern half for use in chlorin synthesis. The conversion entails 1-acylation followed by 9-bromination. The acylation is best achieved by treatment of the Eastern half with a Grignard reagent (EtMgBr or mesityl-MgBr) followed by a 2-pyridyl thioate (Mukaiyama reagent) as described by Rao, P. D. et al., *J. Org. Chem.* 2000, 65, 1084-1092. Such 1-acyldipyrromethanes can be isolated through the use of a dialkylboron complexation method (Muthukumaran, K. et al., *J. Org. Chem.* 2004, 69, 5354-5364.). The bromination is best achieved with N-bromosuccinimide at −78° C. as described by Taniguchi, M. et al., *J. Org. Chem.* 2001, 66, 7342-7354. The conditions for converting dipyrromethane of Formula IV to an Eastern half are rather mild, and consequently, are tolerant to a broad range of substituents in the swallowtail motif.

Compounds of Formula I and Formula Va, Vb may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II), Ni(II), and Au(III). Where the metal is trivalent or tetravalent a counterion is included as necessary in accordance with known techniques.

Linking groups for conjugates. Linking groups are included in compounds of Formula I to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R" is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc., acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212,093; and 6,208,553.

Conjugates. Other groups can be attached to the active compounds to form a conjugate by means of a linking group to tune or adjust the solubility properties of the active compounds, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the active compound or attached by means of an intervening group such as a hydrophilic group, depending upon the particular linking group employed (as noted above).

Hydrophilic groups. Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface attachment groups. As noted above, compounds of the invention can be substituted with a surface attachment group, which may be in protected or unprotected form. A surface attachment group may be a reactive group coupled directly to the active compound, or coupled to the active compound by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl) phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl) phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl); 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl, 1,2-tellurylethyl, 1,3-tellurylpropyl, 2-(4-tellurylphenyl)ethynyl, 4-(2-(4-tellurylphenyl)ethynyl)phenyl, 4-tellurylmethylphenyl, 4-(2-tellurylethyl)phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl)methyl,2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl) methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto) phosphoryl)methyl]phenyl, 4-[2-(hydroxy(mercapto) phosphoryl)ethyl]phenyl, 4-[2-[4-(hydroxy(mercapto) phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl] ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl,4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir,* 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]
  methyl}phenyl,
1,1,1-tris[4-dihydroxyphosphorylmethyl)phenyl]methyl,
  and
4-{1,1,1-tris[4-(dihydroxyphosphorylmethyl)phenyl]
  methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl, 4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.
Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl,
Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc.,
Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc.,
Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.
Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and
Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfonic acids and boronic acids.

Active compounds of the invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Utility. The methods and intermediates described herein are useful for the synthesis of compounds of Formula I as described herein. Such compounds are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al. and as set forth in further detail below.

Stability. An advantage of some embodiments of bacteriochlorin compounds of the present invention is their stability and absorption characteristics. Thus, the present invention provides a "neat" composition consisting of an active compound of the invention (e.g., compounds of Formula I, or the pharmaceutically acceptable salts, prodrugs, or conjugates thereof (e.g, with a targeting agent such as a protein, peptide or antibody)), wherein the composition has or is characterized by a peak Molar absorption coefficient in solution of at least 10,000, up to 300,000 $M^{-1}$ $cm^{-1}$ or more, at a wavelength between 650 and 850 or 900 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g., compounds of Formula I, or the pharmaceutically acceptable salts, prodrugs, or conjugates thereof (e.g, with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}$ $cm^{-1}$ or more, at a wavelength between 650 and 850 or 900 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, have or exhibit a loss of not more than 10, 15 or 20 percent by weight of the bacteriochlorin compound of the invention (due to degredation thereof) when stored in a sealed vessel (e.g., a flask ampoule or vial), at room temperature in the absence of ambient light for at least 3 or 4 months. Degredation can be determined by spectroscopy, thin-layer chromatography, NMR spectroscopy, and/or mass spectrometry, in accordance with known techniques.

Solubility. An advantage of some embodiments of compounds of the invention is their solubility. Thus the present invention provides compositions, including but not limited to pharmaceutical formulations, comprising, consisting of or consisting essentially of: (a) an aqueous solvent (for example, distilled water, saline solution, buffer solution); and (b) from 1, 2, 5 or 10 microMolar up to 200, 300, or 500 milliMolar of an active compound as described herein solubilized in the aqueous solvent.

2. Pharmaceutical Formulations.

Formulation of Pharmaceutical Compositions. The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration. In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358, 603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(loweralkyl)acetals of loweralkyl aldehydes such as acetaldehyde diethyl acetal.

3. Injectables, Solutions and Emulsions. Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders. Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration. Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for other Routes of Administration. Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010,715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations. The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes. In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Ligands. In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alfa, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis*, Pneumococcus, *Hemophilis influenzae B, Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to ligands. Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyldithio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin $e_6$ in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine ε-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

3. Methods of Use.

A. Methods of PDT, Diagnostic and Therapeutic Applications. Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 umol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of opportunistic infections. Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of burns. Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis. Compounds, compositions and methods of the invention are useful for the PDT treatment of subjects afflicted with opportunistic infections of *Vibrio vulnificus*. *V. vulnificus*, a gram-negative bacterium, causes primary sepsis, wound infections, and gastrointestinal illness in humans.

(iv) Ulcers. Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal disease. Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis. Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Active compounds targeted to such inflammatory macrophages are useful for PDT of vulnerable plaque.

(vii) Cosmetic and dermatologic applications. Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne, Compounds, compositions and methods of the invention are useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious diseases. Compounds, compositions and methods of the invention are useful in PDT to treat infectious diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue sealants. Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic disease. Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents. In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolution yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions. In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent. The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

3. Flow cytometry.

Flow cytometry is known and described in, for example, U.S. Pat. Nos. 5,167; 5,915,925; 6,248,590; 6,589,792; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The active compounds described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

The present invention is explained in greater detail in the following non-limiting Examples.

EXPERIMENTAL

We herein report the synthesis of trans-AB-porphyrins bearing one conjugatable group and one swallowtail motif. In addition, the porphyrin bearing the bromo substituent can serve as a benchmark molecule, allowing the determination of the extent to which the swallowtail motifs are responsible for the water solubilization without the polar, ionizable carboxylic acid. Taken together, this work establishes the foundation for the rational synthesis of compact porphyrins for applications where water-solubility and bioconjugation are required.

Results and Discussion

1. Synthesis

The specific target porphyrins are of the trans-AB-type, bearing one swallowtail substituent and one bioconjugatable group, and no substituents at the flanking meso positions (Chart 2).

Chart 2

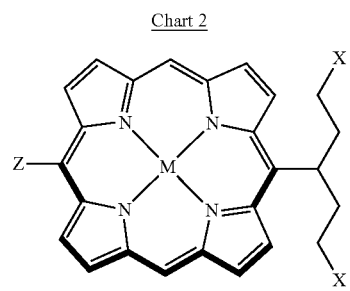

X: polar terminal group
Z: bioconjugatable handle
M: metal

We recently developed two rational routes to trans-AB-porphyrins: (1) Reaction of a 1,9-bis(N,N-dimethylaminomethyl)dipyrromethane+a dipyrromethane in the presence of zinc acetate in ethanol followed by oxidation with DDQ,[21] and (2) reaction of a bis(alkyliminomethyl)dipyrromethane+a dipyrromethane in the presence of zinc acetate in ethanol.[22] Both routes directly afford zinc porphyrins; the latter was employed herein. The dipyrromethanes bearing appropriate substituents for preparing the target porphyrins are available via a one-flask reaction of an aldehyde and excess pyrrole.[23]

A. Dipyrromethanes. The synthesis of the swallowtail dipyrromethanes is shown in Scheme 1. The synthesis begins with 2-bromoethanol. Some intermediates in the synthesis have been described in the literature but without complete characterization data.[24] The complete synthesis is described as follows.

2-Bromoethanol (1) was protected by reaction with tert-butyldimethylsilyl chloride in a mixture of imidazole and DMF (Scheme 1). Aqueous work-up followed by bulb-to-bulb distillation afforded the TBDMS-protected species 2 in 97% yield. A swallowtail nitrile was described by de Groot as a side-product in the alkylation of acetonitrile.[24] We modified the de Groot method by changing the ratios of reactants and by performing the alkylation in a two-step one-flask process. Thus, treatment of acetonitrile with LDA in the presence of HMPA followed by 2, and repetition of this sequence afforded the dialkylated nitrile as the major product. Silica column chromatography gave 3 in 77% yield, along with mono- and trialkylated nitriles, and a small amount of recovered 2. Reduction of 3 with DIBALH at −78° C. in dry toluene gave 4. Aldehyde 4 reacted with excess pyrrole in the presence of InCl₃ catalyst to give the 5-substituted dipyrromethane 5 in 96% yield as a pale yellow, viscous oil.

Scheme 1

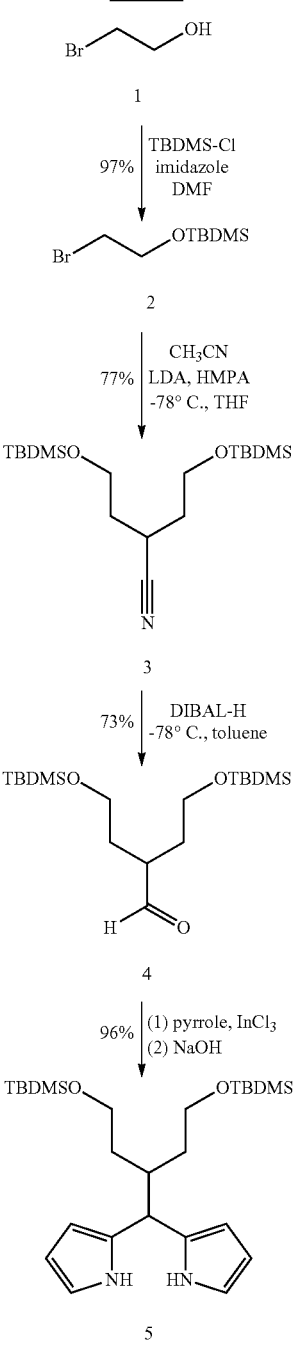

The bioconjugatable site was constructed from 4-hydroxybenzaldehyde by O-alkylation with tert-butyl bromoacetate (Scheme 2). The alkylation proceeded smoothly in anhydrous acetonitrile in the presence of potassium carbonate and a catalytic amount of sodium iodide. Conventional aqueous-organic work-up followed by silica column chromatography afforded 6a as a white, crystalline solid in excellent yield. The aldehyde 6a was reacted with excess pyrrole in the presence of InCl₃. Dipyrromethane 7a was isolated after silica column chromatography as a pale yellow, viscous liquid. Vilsmeier formylation of 7a followed by basic work-up and chromatography on neutral alumina gave the 1,9-diformyldipyrromethane 8a. Yields were generally low (25-45%), presumably because of the sensitivity of the tert-butyl ester to the formylation conditions. For characterization purposes the dibutyltin complex 8aSnBu$_2$ was prepared by derivatization of 8 and dibutyltin dichloride in a standard reaction.[25] A similar sequence of reactions led from 4-bromobenzaldehyde 6b to diformyldipyrromethane 8b. Yields were comparable to those obtained for the tert-butyl ester derivatives, with the exception of the Vilsmeier formylation, which provided 8b in excellent yields. Treatment of 8a or 8b with excess propylamine at room temperature quantitatively afforded the bis-imine 9a or 9b, respectively.

Scheme 2

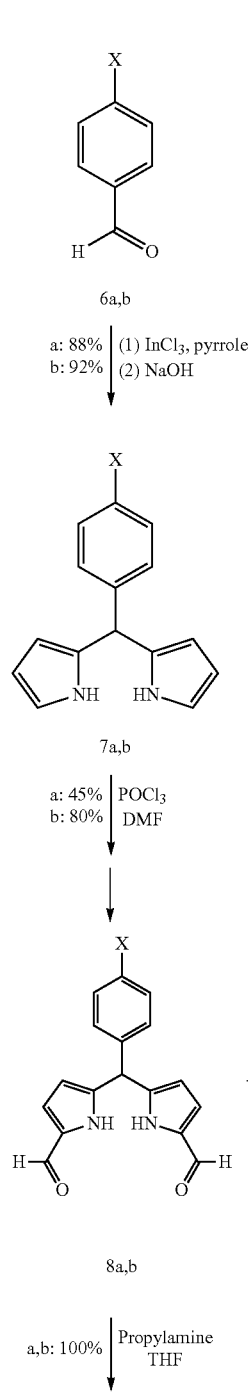

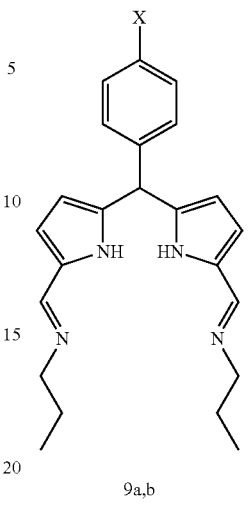

9a,b a: X = OCH$_2$COO$^t$Bu
b: X = Br

B. Porphyrin-phosphates. The condensation of the swallowtail dipyrromethane 5 and the bis(imino)dipyrromethane 9a or 9b was carried out in the presence of a ten-fold excess of anhydrous zinc acetate in refluxing dry toluene open to the air (Scheme 3). In the original publication,[22] ethanol was the solvent of choice for porphyrin formation. Ethanol proved to be an excellent solvent for the synthesis of the 4-bromophenyl-substituted porphyrin (10b), affording the desired product in 24-27% yield. However, under the same conditions only very small amounts of 10a were isolated. The main side-reaction was hydrolysis of the tert-butyl ester. Some of the free carboxylate was re-esterified by the solvent, as shown by LD-MS analysis of the crude reaction mixture and by $^1$H NMR analysis of the pure porphyrin. Therefore small-scale trial reactions were carried out in a number of solvents to find a substitute for ethanol. Chloroform resulted both in very low yields and extensive scrambling (i.e., formation of other porphyrin products). Upon reaction in dry toluene, scrambling was not observed and both 10a and 10b could be isolated after straightforward silica column chromatography. Treatment of 10a and 10b with TBAF solution in THF cleaved the TBDMS protecting groups and also caused some demetalation of the zinc porphyrin, affording a mixture of the zinc chelate and the free base porphyrin as shown by LD-MS. Remetalation with zinc acetate followed by chromatography on neutral alumina gave the zinc-porphyrin-diols 11a and 11b in excellent (>80%) yield. It is important to minimize the reaction time for 10a→11a, as prolonged exposure under these conditions results in hydrolysis of the tert-butyl ester groups.

Scheme 3

5 + 9a, b

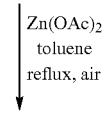

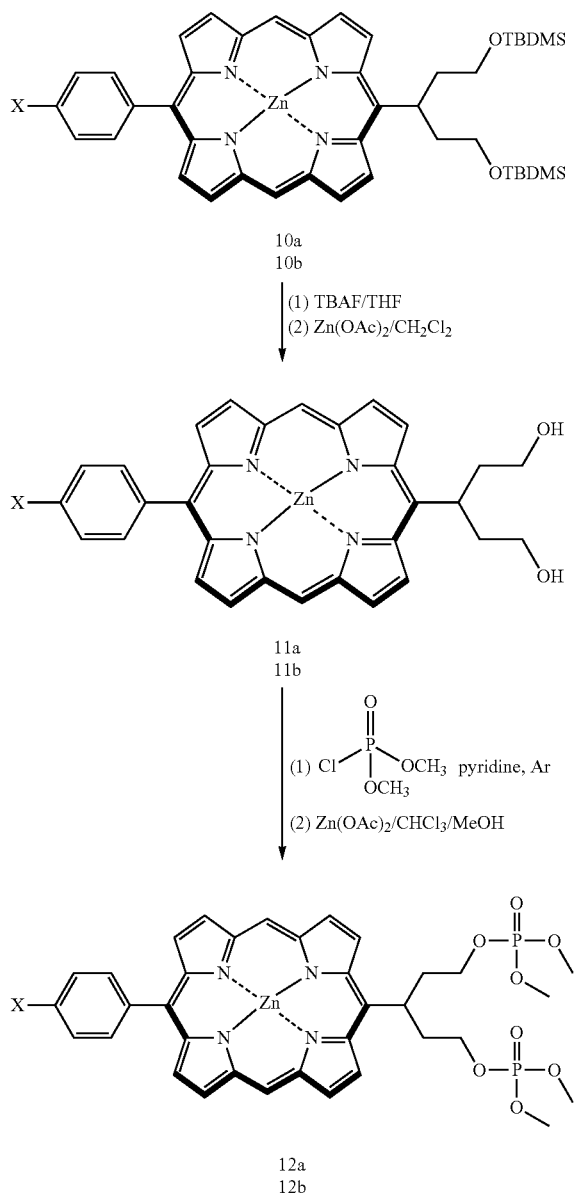

10a
10b (1) TBAF/THF
(2) Zn(OAc)$_2$/CH$_2$Cl$_2$ 11a
11b (1) Cl-P(=O)(OCH$_3$)(OCH$_3$) pyridine, Ar
(2) Zn(OAc)$_2$/CHCl$_3$/MeOH 12a
12b a: X = OCH$_2$COO$^t$Bu
b: X = Br Porphyrin-diols 11a and 11b are highly polar and are only sparingly soluble in most organic solvents. Reaction of 11a with dimethyl chlorophosphate in anhydrous pyridine gave no 12a, whereas similar reaction with 11b gave a very low yield of 12b. The poor yields are presumably due to the combination of low solubility and low reactivity on the part of the porphyrin-diol starting materials. We assumed that incorporation of the dimethoxyphosphoryl groups at an earlier stage could provide a more efficient process.

Our attempts to introduce the phosphate groups at the aldehyde stage were unsuccessful. Phosphorylation of the hydroxy groups of aldehyde 4 appears attractive, but deprotection of 4 affords the monocyclic hemiacetal and the bicyclic acetal of the corresponding 3-formylpentane-1,5-diol as an approximately 1:2 equilibrium mixture. None of the free diol was observed by $^1$H NMR spectroscopy. Therefore the phosphate groups were introduced at the dipyrromethane stage (Scheme 4). Treatment of the TBDMS-protected swallowtail dipyrromethane 5 with TBAF in THF at room temperature resulted in cleavage of the protecting groups. Aqueous-organic work-up followed by chromatography on neutral alumina gave the dipyrromethane-diol 5-(OH)$_2$ as a pale yellow oil in 89% yield. The dipyrromethane-diol 5-(OH)$_2$ was reacted with dimethyl chlorophosphate in anhydrous CH$_2$Cl$_2$ to give the bis(dimethoxyphosphoryloxy)dipyrromethane 5-(P)$_2$ as a yellow oil in 61% yield. A small amount (20-30% of the total) of monophosphate derivative 5-(P/OH) was also isolated, and could be transformed to 5-(P)$_2$. Alternatively, 5-(P/OH) could prove useful if a second functional group is to be introduced into the swallowtail moiety.

Reaction of 5-(P)$_2$ with bis-imine 9a or 9b in anhydrous toluene in the presence of ten equivalents of zinc acetate furnished the corresponding zinc porphyrin 12a or 12b as a dark purple solid in ~15% yield (Scheme 5). Two problems were encountered in handling the porphyrin-phosphate compounds 12a and 12b: (1) hydrolysis of the phosphates during purification, and (2) hydrolysis of the phosphates during "standard" conditions for methyl ester hydrolysis.[26] The observations concerning these problems are described in more detail as follows.

Scheme 4

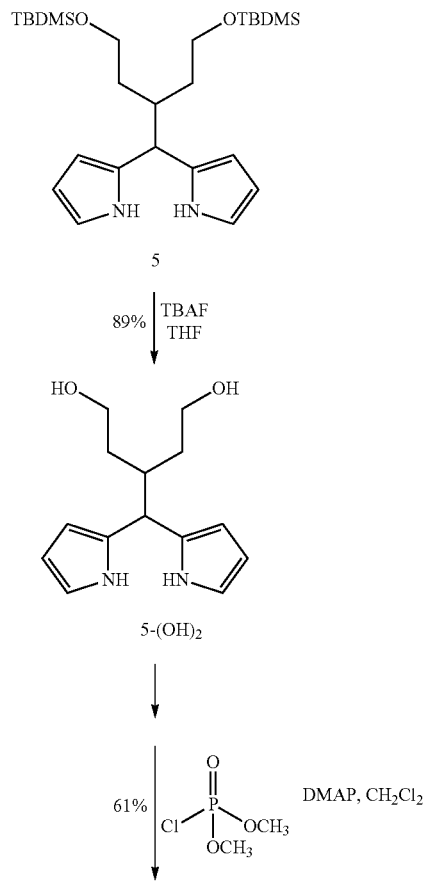

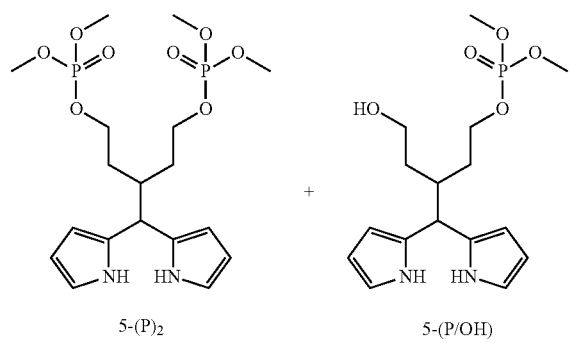

5-(P)$_2$     5-(P/OH)

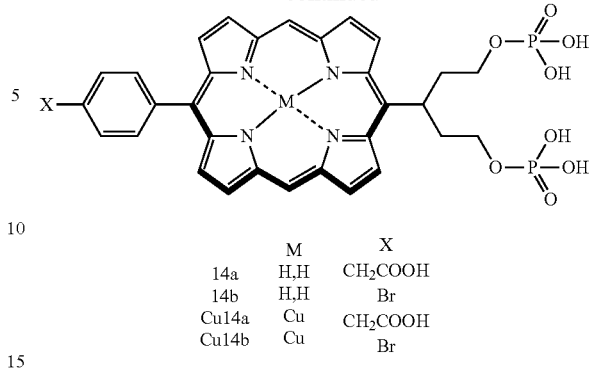

| | M | X |
|---|---|---|
| 14a | H,H | CH$_2$COOH |
| 14b | H,H | Br |
| Cu14a | Cu | CH$_2$COOH |
| Cu14b | Cu | Br |

Scheme 5

5-(P)$_2$ + 9a, b

Zn(OAc)$_2$
toluene
reflux, air

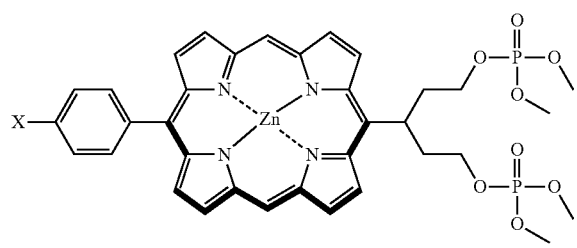

12a: X = OCH$_2$COO$^t$Bu (22%)
12b: X = Br (21%)

TFA/CH$_2$Cl$_2$

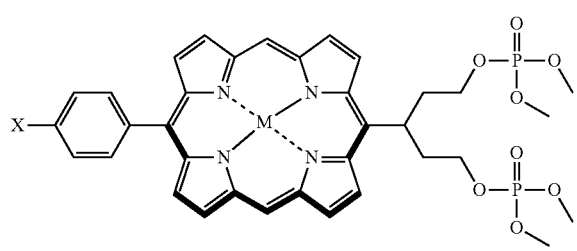

13a, M = H,H (76%)
13b, M = H,H (98%)

Cu(OAc)·H$_2$O
CH$_2$Cl$_2$/MeOH

Cu13a, M = Cu (98%)
Cu13b, M = Cu (99%)

(1) TMS-Br, CH$_2$Cl$_2$
(2) MeOH

B.1. Unexpected Reactions of Porphyrin-phosphates. Although the isolated yields of 12a and 12b were reasonable, the spectroscopic yields were higher (30-45%). It is likely that some losses occur during the chromatographic purification. The elution mixture contains a protic solvent (methanol), which can result in the decomposition of the phosphate-functionalized swallowtail groups in the presence of a zinc central atom (vide infra). This is supported by the fact that during the elution a number of porphyrinic species are observed, none of which were observed upon LD-MS analysis of the crude sample. Performing most of the elution with a mixture of ethyl acetate/CH$_2$Cl$_2$, followed by MeOH/CH$_2$Cl$_2$ resulted in an increase in the yield to 22% for 12a.

Porphyrin 12a contains both the bioconjugatable site and the water-solubilizing groups, masked by tert-butyl and methyl esters, respectively. Attempts at the simultaneous removal of the tert-butyl and methyl ester protecting groups with TMS-Br were unsuccessful. A series of test reactions carried out on 12b revealed that the phosphate groups were susceptible to displacement by bromide, as indicated by LD-MS analysis of the crude reaction mixture, and LD-MS and $^1$H NMR spectroscopic analysis of the pure porphyrin product. This compound is identical to 15b (vide infra). When the reactions were conducted at room temperature as opposed to refluxing chloroform, in the presence of only a slight excess of TMS—Br, the bromination was suppressed, but the isolation of the desired compound bearing unprotected phosphate groups proved challenging. The following observations were made:

(1) The crude porphyrin-phosphates, while displaying excellent water-solubility initially, precipitated out of solution within minutes.

(2) Because TMS-Br removed some of the zinc, remetalation was attempted with zinc acetate. This resulted in the immediate and quantitative precipitation of the porphyrinic species from the solution. Most (but not all) of the precipitate could be redissolved in concentrated (15 wt %) aqueous NaOH.

(3) When 12b was treated with TMS-Br in the presence of TEA to suppress demetalation,[27] the deprotected porphyrin-diol 11b was not formed until the addition of a protic solvent. During the work-up, 11b formed in quantitative yield, as determined by $^1$H NMR spectroscopy and LD-MS [obsd m/z 567, calcd 566 for demetalated (M+H)$^+$] of the purified sample.

(4) A sample of 12b in a mixture of CDCl$_3$/CD$_3$OD was monitored by $^1$H NMR and LD-MS. Within 8 h the formation of porphyrin 11b was almost quantitative (obsd m/z 566, disappearance of phosphate methyl ester singlets).

(5) Basic hydrolysis (H$_2$O/MeOH, NaOH, various concentrations) removed only two of the methyl esters, but none of 11b was formed.

These observations suggested that the zinc atom plays a pivotal role in the displacement of the phosphate groups, both during purification of the crude porphyrin-forming reaction mixture and upon deprotection with TMS-Br. Without wishing to be bound to any particular theory, it is believed that the coordination of one of the phosphate oxygens to the apical site of the zinc ion renders the phosphorous atom susceptible to attack by nucleophiles, resulting in the cleavage of the indicated O—P bond. Zinc ion is well known to promote phosphate hydrolysis in biological systems.[28] This geometry in unavailable if the fifth coordination site of the metal is occupied by a different electron pair donor, e.g. OH$^-$, which explains why 11b was not observed during basic hydrolysis. It is also possible that an additional coordination event takes place upon the addition of zinc to the sample (point 2 above). The zinc metal may coordinate the phosphate groups making them inaccessible for the solvent, which results in precipitation of the porphyrin. Addition of concentrated aqueous NaOH dissolves the precipitate because the large excess of OH— ions disrupts the zinc-O-phosphate complex.

In summary, zinc porphyrins bearing phosphate-terminated swallowtail groups were not obtained for the pent-3-yl groups examined. Accordingly, we turned our attention to free base and copper analogues of the porphyrin-phosphates.

B.2. Preparation of Free Base or Copper Chelates of Porphyrin-phosphates. To avoid zinc-mediated hydrolysis of the phosphate group, the free base porphyrins 13a and 13b were prepared by demetalation of 12a and 12b, respectively, by treatment with a 1:1 mixture of TFA and CH$_2$Cl$_2$. The demetalation was essentially complete within 15 min (as determined by absorption spectroscopy), but 12a was allowed to react further to allow for the quantitative cleavage of the tert-butyl ester. Treatment of the free base porphyrins (13a,b) with copper acetate afforded the corresponding copper porphyrins (Cu13a,b). Copper is strictly four-coordinate and was not expected to facilitate phosphate hydrolysis. Compounds Cu13a and Cu13b were only characterized by LD-MS, FAB-MS and absorption spectroscopy because of the difficulties associated with the $^1$H NMR spectroscopy of Cu-containing samples.

Deprotection of the free base porphyrins (13a,b) and copper porphyrins (Cu13a,b) was carried out using TMS-Br. The free base porphyrin 13b reacted smoothly with a slight excess of TMS-Br in dry CH$_2$Cl$_2$ at room temperature. Subsequent treatment with aqueous NaOH and reverse-phase column chromatography yielded the desired porphyrin-diphosphate 14b in excellent yield. The carboxylate-functionalized 13a required a large excess of TMS-Br, whereupon the desired fully deprotected target porphyrin-phosphate was obtained in 92% purity. The remaining 8% impurity was identified as the mono-methyl intermediate.

The copper complexes were only partially deprotected by the same amount of TMS-Br as for the corresponding free base porphyrins. ESI-MS showed the dimethyl- and monomethyl- Cu14ab as the major products. Increasing the amount of TMS-Br resulted in almost complete demetalation and a reduction in the deprotection yield. Small quantities of Cu14a and Cu14b could be isolated but the samples were only partially characterized. It is worth noting that neither diol 11a nor 11b (nor copper chelates thereof) was observed by LD-MS or ESI-MS during the deprotection reaction; this result is as expected if central metal atom coordination promotes hydrolysis (as proposed for the instability of 12ab and 14ab). It is also worth mentioning that even the partially deprotected copper chelates display excellent water-solubility (>10 mM). In summary, the free base and copper porphyrin phosphates were prepared without the complications of loss of phosphate encountered with corresponding zinc chelates.

C. Porphyrin-phosphonates. It was expected that in vivo the phosphate groups may be susceptible to cleavage by phosphatases. Therefore porphyrin-phosphonates, which are stable to phosphatases, were prepared from the porphyrin-diols 11a and 11b (Scheme 6). Montforts has reported the conversion of a porphyrin-alcohol to the corresponding bromide upon reaction with CBr$_4$ and triphenylphosphine.[29] Similar treatment of a thoroughly dried (overnight, room temperature, 0.05 mmHg) sample of 11a or 11b in anhydrous CH$_2$Cl$_2$ with CBr$_4$ at 0° C., followed by excess triphenylphosphine afforded the corresponding free base dibromo-porphyrin 15a or 15b in excellent yield. Refluxing 15a or 15b in neat (MeO)$_3$P under an inert atmosphere for 36 h afforded 16a or 16b in moderate to good yield as a dark red solid. The reaction also produced the intermediate monobromo, monophosphonate-porphyrins (16a-Br, 16b-Br). Although yields have been optimized for the production of 16a and 16b; it is possible that the intermediates could be obtained in good yields and serve as starting points for the introduction of two different polar groups into one molecule.

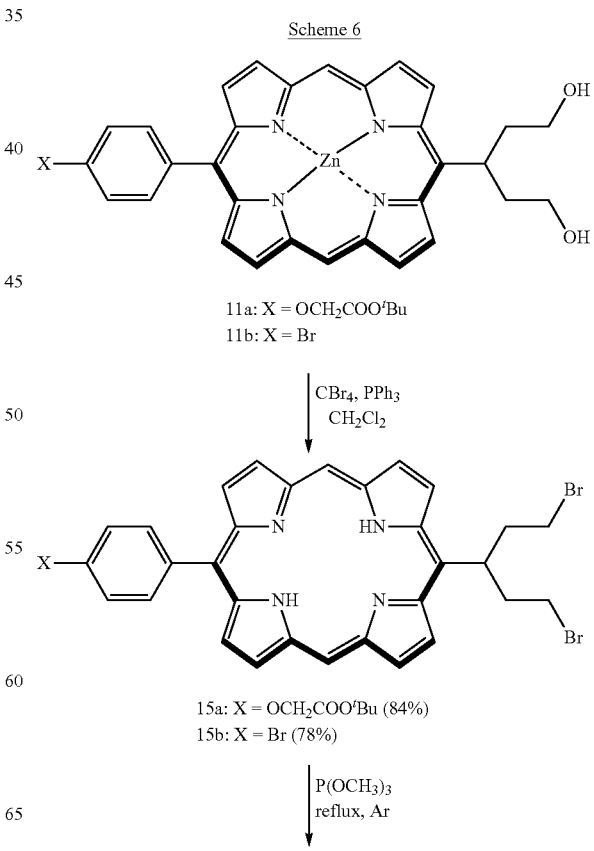

Scheme 6

11a: X = OCH$_2$COO$^t$Bu
11b: X = Br

CBr$_4$, PPh$_3$
CH$_2$Cl$_2$

15a: X = OCH$_2$COO$^t$Bu (84%)
15b: X = Br (78%)

P(OCH$_3$)$_3$
reflux, Ar

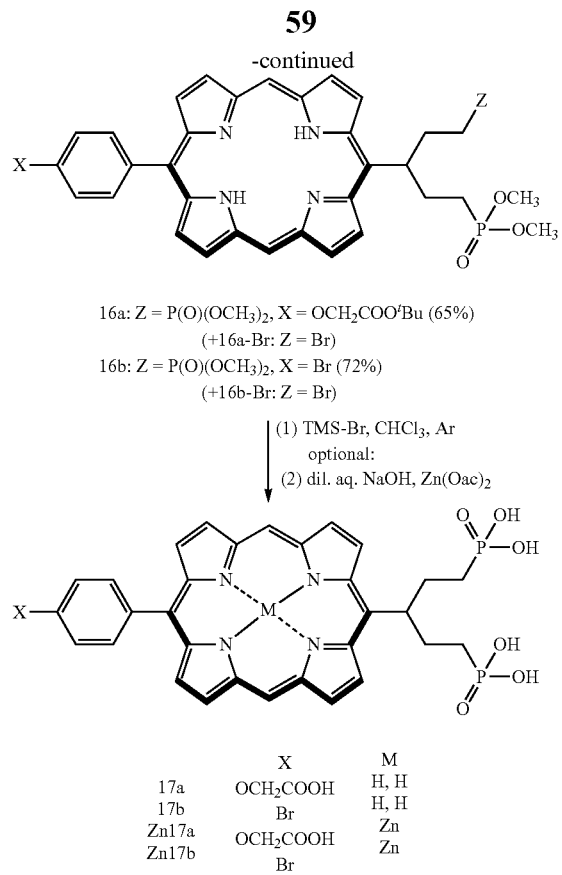

16a: Z = P(O)(OCH₃)₂, X = OCH₂COO$^t$Bu (65%)
(+16a-Br: Z = Br)
16b: Z = P(O)(OCH₃)₂, X = Br (72%)
(+16b-Br: Z = Br)

(1) TMS-Br, CHCl₃, Ar
optional:
(2) dil. aq. NaOH, Zn(Oac)₂

| | X | M |
|---|---|---|
| 17a | OCH₂COOH | H, H |
| 17b | Br | H, H |
| Zn17a | OCH₂COOH | Zn |
| Zn17b | Br | Zn |

Cleavage of the methyl and tert-butyl esters simultaneously was investigated by treatment of 16a or 16b with excess TMS-Br in refluxing chloroform under argon. The free acids were isolated after methanolysis of the silyl intermediates. The green solids obtained after treatment with methanol were insoluble in a number of organic solvents and water. Addition of small quantities of dilute aqueous base (NaOH or NaHCO₃) rendered the porphyrins water-soluble. Treatment of the basic porphyrin solutions (prior to purification) with zinc acetate resulted in formation of the corresponding zinc chelates. Purification of each free base or zinc porphyrin was achieved by reversed phase column chromatography upon elution with water/methanol. Removal of the solvent followed by freeze-drying of the aqueous samples yielded the desired porphyrin (17a, 17b, Zn17a, Zn17b) in good to excellent yield.

2. Characterization and Water-Solubility

All of the hydrophobic porphyrins were analyzed in neat form by laser desorption mass spectrometry (LD-MS), FAB-MS, as well as $^1$H NMR spectroscopy (except copper chelates) and absorption and emission spectroscopy. All of the deprotected porphyrin-phosphates and porphyrin-phosphonates were characterized by $^1$H NMR spectroscopy, ESI-MS, and absorption and emission spectroscopy. The ESI spectra exhibited a strong peak due to the parent molecule (protonated and sodium adduct in the positive-ion mode; deprotonated in the negative-ion mode), with no peaks owing to partially deprotected porphyrins. Each deprotected porphyrin sample was found to be homogeneous upon examination by reverse-phase HPLC (see Experimental Section).

All of the porphyrin-phosphates and porphyrin-phosphonates examined herein were readily soluble in water across a wide pH-range, and exhibited sufficient solubility to enable $^1$H NMR measurements in D₂O (not shown). Although good quality $^1$H NMR spectra were obtained at room temperature, the resolution increased substantially upon increasing the temperature to 60° C. The higher temperature also enabled observation of the OCH₂ signal in the carboxylic acid, which at room temperature is coincident with the water signal. gCOSY experiments carried out on the porphyrin-phosphonates enabled the partial assignment of the signals.

Determination of the upper limit of water-solubility was not possible due to the lack of material; however, in each case examined, 8-10 mg of pure porphyrin (14b, 17b, Zn17b, 17a, Zn17a) completely dissolved in 300 µL of distilled water, consistent with a concentration of >20 mM. The aqueous solutions are stable for days at room temperature when shielded from the light. Neither precipitation nor aggregation was observed either with the naked eye or by absorption spectroscopy.

3. Structural Studies

The success of the hydrocarbon swallowtails in the lipophilization of extended aromatic systems was explained by projection of the alkyl groups above and below the plane of the macrocycle (not shown). This projection prevents π-π stacking and aggregation. EPR measurements on the radical cation of an all-hydrocarbon swallowtail porphyrin suggested that this was indeed the case and the swallowtail branches were projecting above and below the porphyrin plane.

We carried out $^1$H NMR studies (1 and 2D NMR, VT NMR) of a series of swallowtail porphyrins that were synthesized in this work to gain further insight concerning conformation of the swallowtail groups (Chart 3). The results are as follows.

The $^1$H NMR spectrum of the A₄-swallowtail porphyrin in CDCl₃ (18 and Zn18, synthesized from 4 via a standard procedure[19]) contains two broad apparent singlets (~9.67 ppm and ~9.49 ppm) in the aromatic region each with integration of 4. This is somewhat surprising, as symmetry considerations would suggest the appearance of one singlet in the aromatic region with an integration of eight, the eight β-protons being equivalent. The signal corresponding to the CH protons of the swallowtail motifs (the branch site C$^1$'H) appears as a broad, structureless multiplet (~5.56 ppm). NOESY experiments revealed that the two types of aromatic protons were close to each other in space, and also that the one giving rise to the 9.67 ppm signal is close to C$^1$'H.

At room temperature in toluene-d₈, the spectrum of 18 was similar to that recorded in CDCl₃, although the signal at higher field consisted of two overlapping broad singlets. Increasing the temperature resulted in the broadening of the two aromatic signals (9.60 ppm and 9.93 ppm). At ~70° C. the two signals collapsed into one broad singlet (9.77 ppm), which eventually became a sharp singlet (9.72 ppm, 90° C.) with an integration=8. A similar but less pronounced sharpening was observed for the broad singlet at −1.72 ppm (NH) and the multiplet of C$^1$'H (5.88 ppm) (not shown).

The trans-AB porphyrins examined (10b and 12b) have nominally lower symmetries than the A₄-porphyrins 18 and Zn18. A trans-AB porphyrin with simple A and B substituents is expected to exhibit five $^1$H signals in the aromatic region stemming from the four porphyrin β-positions and the unsubstituted meso position. However, the $^1$H NMR spectra of all swallowtail trans-AB porphyrins studied in this work are more complex. Typically, two separate meso proton signals are observed (at approx. 10.0 and 10.1 ppm). The four β protons on the swallowtail-side appear as two doublets (around 9.7 and 9.5 ppm) with different coupling constants, and another pair of doublets at ~9.30 ppm (overlapping). Raising the temperature again simplifies the spectrum, whereupon (1) the two meso-proton signals collapse into one singlet (~100° C., δ10.03 ppm), and (2) the doublets corresponding to C³H and C⁷H broaden out and move closer to each other, although in the available temperature range (up to 100° C.) they remain separate signals. Similarly to the A₄-porphyrin, NOESY experiments showed the proximity between C¹'H and one of either C³H or C⁷H. Two of the four C²'H₂ protons are pointing toward the other swallowtail-flanking β proton (not shown).

These results suggest that the swallowtail alkyl groups not only preferentially occupy positions out-of-plane with the porphyrin ring, but at room temperature are hindered in their rotation around the carbon-carbon single bond between the porphyrin meso position and the swallowtail branching site (i.e., C⁵—C¹'H). The C¹'H is more or less in the plane of the porphyrin macrocycle. This conformation results in the two sets of β-protons and the two different meso ¹H signals. At increased temperature the rotational barrier is more easily surmounted and the $C_2$ symmetry of the porphyrin is restored. This geometry undoubtedly helps suppress cofacial interaction between porphyrin molecules at room temperature, thereby increasing solubility. The results of the NMR experiments are consistent with previous observations obtained via EPR spectroscopy, and provide additional evidence concerning the conformation of the swallowtail porphyrins in solution.

Experimental Section

General Procedures. ¹H NMR (300 MHz) and ¹³C NMR (75 MHz) spectra were recorded in CDCl₃ unless noted otherwise. Bulb-to-bulb distillation was performed using a standard-size Kugelrohr apparatus. Absorption spectra and fluorescence spectra were collected at room temperature in CH₂Cl₂ unless noted otherwise. Infrared absorption spectra were recorded as thin films. Hydrophobic porphyrins were analyzed in neat form by laser desorption mass spectrometry (LD-MS). The water-soluble porphyrins were analysed by direct infusion of water/methanol (40:60) solutions by atmospheric pressure electrospray mass spectrometry (ESI-MS). Both in LD-MS and ESI-MS analyses, positive ions were detected unless noted otherwise. Melting points are uncorrected. Solvents were dried according to standard procedures. LDA was generated in situ.[30] All other chemicals were used as received from commercial sources.

Chromatography. Preparative chromatography was performed using silica or alumina (80-200 mesh). Thin layer chromatography was performed on silica or alumina. Samples were visualized by UV-light (254 nm and 365 nm), Br₂-vapor or KMnO₄/K₂CO₃. Dipyrromethanes and compounds 2-4 and 6a were analyzed by GC as described previously.[23] Reversed phase preparative column chromatography was carried out using C-18-coated silica and eluants based on water admixed with methanol. Analytical RP-HPLC was carried out using a HPLC system [Hypersil C-18 column (5 μm, 125 mm×4 mm); A=water (0.1% TFA), B=acetonitrile (0.1% TFA); detection @ 254, 410 and 417 nm].

2-(tert-Butyldimethylsilyloxy)ethyl bromide (2). Following a published procedure,[24] 2-bromoethanol (10.0 mL, 141 mmol) was added to a mixture of imidazole (12.5 g, 184 mmol) and tert-butyldimethylsilyl chloride (21.1 g, 140 mmol) in anhydrous DMF (25 mL). The reaction mixture was stirred at room temperature for 12 h. Water and diethyl ether were added. The phases were separated. The aqueous phase was extracted with diethyl ether. The combined organic phases were washed with water and brine. The solution was dried (Na₂SO₄). Evaporation of the solvent followed by bulb-to-bulb distillation (40-45° C./0.05 mmHg) yielded a colorless liquid (32.5 g, 97%): IR (film, $\nu_{max}$ cm⁻¹) 2951, 2859, 1471; ¹H NMR δ 0.07 (s, 6H), 0.89 (s, 9H), 3.36-3.41 (m, 2H), 3.85-3.90 (m, 2H); ¹³C NMR δ −5.06, 18.49, 26.04, 33.45, 63.74; EI-MS 137/139, 181/183, calcd 238.0389 (C₈H₁₉BrOSi); Anal. Calcd C, 40.17; H, 8.01. Found: C, 40.55; H, 8.25.

3-Cyano-1,5-bis(tert-butyldimethylsilyloxy)pentane (3). A solution of HMPA (12.0 mL) and LDA (33.5 mmol) in dry THF (39 mL) at −78° C. under argon was treated with acetonitrile (1.75 mL, 33.5 mmol). The solution was stirred for 30 min, and 2 (6.82 g, 29 mmol) in THF (30 mL) was added dropwise. Stirring was continued for 2 h, after which a second portion of LDA (33.5 mmol in 39 mL THF) was added. The solution was stirred for 30 min, and 2 (6.82, 29 mmol) in THF (30 mL) was added dropwise. The reaction was allowed to proceed for 2 h. Saturated aqueous NH₄Cl was added, and the mixture was allowed to reach room temperature. Diethyl ether was added, the phases were separated, and the aqueous layer was extracted with diethyl ether. The combined organic phases were washed with water and brine, dried over Na₂SO₄, and concentrated. Column chromatography [silica, petroleum ether/diethyl ether (40:1)] afforded a colorless liquid (7.79 g, 77%): IR (film, $\nu_{max}$ cm⁻¹) 2953, 2859, 1738, 1472; ¹H NMR δ 0.07 (s, 12H), 0.89 (s, 18H), 1.76-1.83 (m, 4H), 3.03-3.13 (m, 1H), 3.73-3.83 (m, 4H); ¹³C NMR δ −5.24, 18.45, 24.82, 26.09, 35.32, 60.08, 122.15; EI-MS 115, 142/144, 156/157, 182/184, 198, calcd 357.2519 (C₁₈H₃₉NO₂Si₂); Anal. Calcd C, 60.44; H, 10.99; N, 3.92. Found C, 60.53; H, 11.24; N, 4.00.

3-Formyl-1,5-bis(tert-butyldimethylsilyloxy)pentane (4). Following a published procedure,[24] a solution of 3 (3.65 g, 10.2 mmol) in dry toluene (52 mL) at −78° C. under argon was treated with DIBALH (12 mmol, 8.3 mL, 1.5 M solution in toluene), and the reaction was allowed to proceed for 1 h. Water (2.6 mL) was added, and the mixture was allowed to reach room temperature. Aqueous NaOH (2.6 mL, 4.0 M solution) was added, and stirring was continued for 15 min. Water (7.8 mL) was added and the suspension was stirred for a further 15 min. The sample was dried (Na₂SO₄), concentrated at reduced pressure, and chromatographed [silica, petroleum ether/diethyl ether (20:1)], affording a colorless liquid (2.70 g, 73%): IR (film, $\nu_{max}$ cm⁻¹) 2955, 2859, 1729, 1708, 1472; ¹H NMR δ 0.01 (s, 12H), 0.87 (s, 18H), 1.64-1.74 (m, 2H), 1.85-1.96 (m, 2H), 2.50 (m, 1H), 3.57-3.68 (m, 4H), 9.65 (d, J=2.4 Hz, 1H); ¹³C NMR δ −5.27, 18.45, 26.09, 32.15, 46.40, 60.80, 204.74; EI-MS 171/172, 141, 97, 75, calcd 360.2516 (C₁₈H₄₀O₃Si₂); Anal. Calcd C, 59.94; H, 11.18. Found: C, 58.15; H, 11.16.

5-[1,5-Bis(tert-butyldimethylsilyloxy)pent-3-yl]dipyrromethane (5). Following a standard procedure,[23] aldehyde 4 (4.61 g, 12.80 mmol) was dissolved in dry pyrrole (89.1 mL, 1.28 mmol), and the solution was flushed with argon for 10 min. InCl₃ (285 mg, 1.28 mmol) was added, and the reaction was allowed to proceed for 3 h. The reaction was quenched by addition of powdered NaOH (1.54 g, 38.5 mmol). The mixture was stirred for 45 min. The mixture was filtered. The filtrate was concentrated at reduced pressure. The residue was chromatographed [silica, ethyl acetate/CH₂Cl₂/hexanes (1:2:7)] affording a viscous, pale yellow liquid (5.87 g, 96%): IR (film, $\nu_{max}$ cm⁻¹) 3427, 1639; ¹H NMR δ 0.09 (s, 12H), 0.94 (s, 18H), 1.35-1.44 (m, 2H), 1.71-1.78 (m, 2H), 2.41-2.43 (m, 1H), 3.64-3.77 (m, 4H), 4.38 (d, J=4.2 Hz, 1H), 6.03 (app s, 2H), 6.13-6.16 (m, 2H), 6.65-6.66 (m, 2H), 8.45-8.55 (br, 2H); ¹³C NMR δ −5.08, 18.65, 26.29, 35.13, 35.37, 40.41, 62.18, 107.03, 108.27, 116.45, 132.25; LD-MS obsd 475.6; FAB-MS obsd 476.3255, calcd 476.3254 (C₂₆H₄₈N₂O₂Si₂); Anal. Calcd C, 65.49; H, 10.15; N, 5.87. Found C, 65.43; H, 10.23; N, 5.73.

5-(1,5-Dihydroxypent-3-yl)dipyrromethane (5-(OH)$_2$). A solution of 5 (3.81 g, 8.01 mmol) in THF (30 mL) was treated with TBAF (4.61 g, 17.6 mmol). The reaction was allowed to proceed until the starting material could not be detected by TLC (alumina, CH$_2$Cl$_2$/MeOH, 3%). The THF was evaporated. The residue was dissolved in a mixture of ethyl acetate and water. The aqueous layer was extracted with ethyl acetate. The combined organic phase was washed with water and dried, (Na$_2$SO$_4$). The solvent was removed and the residue was chromatographed [neutral alumina, CH$_2$Cl$_2$/MeOH (2→10%)] to afford an off-white viscous oil (1.60 g, 89%): $^1$H NMR δ 1.43-1.50 (m, 2H), 1.68-1.79 (m, 2H), 2.39-2.43 (m, 3H), 3.59-3.75 (m, 4H), 4.21 (d, J=5.4 Hz, 1H), 6.04 (d, J=0.9 Hz, 2H), 6.13-6.16 (m, 2H), 6.65-6.66 (m, 2H), 8.40-8.55 (br, 2H); $^{13}$C NMR δ 25.88, 34.86, 35.60, 41.79, 61.25, 106.77, 108.38, 117.03, 131.84; FAB-MS obsd 248.1528, calcd 248.1525 (C$_{14}$H$_{20}$N$_2$O$_2$); Anal. Calcd C, 67.71; H, 8.12; N, 11.28. Found C, 66.59; H, 8.62; N, 10.34.

5-[1,5-Bis(dimethoxyphosphoryloxy)pent-3-yl]dipyrromethane (5-(P)$_2$). A solution of 5-(OH)$_2$ (950 mg, 4.24 mmol) in CH$_2$Cl$_2$ (16 mL) was treated with DMAP (1.18 g, 9.67 mmol) followed by slow addition of a solution of dimethyl chlorophosphate (1.06 mL, 9.83 mmol) in CH$_2$Cl$_2$ (11 mL). The reaction mixture was stirred at room temperature for 8 h. The solution was diluted with CH$_2$Cl$_2$ and water. The aqueous layer was extracted with CH$_2$Cl$_2$. The organic layer was washed with water. The organic layer was dried (Na$_2$SO$_4$), concentrated, and chromatographed [silica, CH$_2$Cl$_2$/MeOH (2→5%)], affording a pale yellow oil (1.19 g, 61%): IR (film, ν$_{max}$ cm$^{-1}$) 3320, 1567; $^1$H NMR δ 1.57-1.64 (m, 2H), 1.84-1.90 (m, 2H), 2.19 (m, 1H), 3.72 (s, 6H), 3.76 (s, 6H), 4.02 (q, J=8.4 Hz, 4H), 4.28 (d, J=5.1 Hz, 1H), 6.00-6.01 (m, 2H), 6.10-6.13 (m, 2H), 6.67-6.69 (m, 2H), 8.79 (br, 2H); $^{13}$C NMR δ 31.16, 32.54, 32.62, 35.21, 40.76, 54.55, 54.65, 66.29, 106.85, 108.32, 117.22, 130.88; FAB-MS obsd 464.1480, calcd 464.1477 (C$_{18}$H$_{30}$N$_2$O$_8$P$_2$); Anal. Calcd C, 46.55; H, 6.51; N, 6.03. Found C, 46.76; H, 6.58; N, 6.03. Data for 5-(P/OH): TLC analysis of the crude mixture revealed the presence of a more polar component, which was isolated as an off-white oil: IR (film, ν$_{max}$ cm$^{-1}$) 3320, 1566, 1450; $^1$H NMR δ 1.45-1.87 (m, 4H), 2.44-2.46 (m, 1H), 3.66 (t, J=5.1 Hz, 2H), 3.75 (s, 3H), 3.78 (s, 3H), 3.95-4.19 (m, 2H), 4.26 (d, J=4.8 Hz, 1H), 6.03 (app s, 2H), 6.14 (app s, 2H), 6.68 (app s, 2H), 8.64 (br, 2H); $^{13}$C NMR δ 33.07, 34.84, 35.23, 41.33, 54.67, 54.73, 65.65, 66.71, 106.65, 106.96, 108.26, 108.34, 111.76, 117.08, 117.15, 131.27, 131.69; EI-MS 157/158, 230/231; FAB-MS obsd 356.2, calcd 356.2 (C$_{16}$H$_{25}$N$_2$O$_5$P); Anal. Calcd C, 53.93; H, 7.07; N, 7.86. Found C, 53.43; H, 7.17; N, 7.63.

4-(tert-Butoxycarbonylmethoxy)benzaldehyde (6a). A solution of 4-hydroxybenzaldehyde (2.44 g, 20.0 mmol) in dry acetonitrile (8.0 mL) was treated with powdered, dried K$_2$CO$_3$ (3.04 g, 22.0 mmol) and NaI (304 mg, 2.00 mmol). The mixture was refluxed under argon for 30 min. tert-Butyl bromoacetate (1.48 mL, 1.95 g, 10.0 mmol) was added dropwise, and the reflux was continued for 12 h. Water and CH$_2$Cl$_2$ were added and the phases were separated. The aqueous layer was extracted with CH$_2$Cl$_2$. The combined organic phase was washed with water. The organic layer was dried (Na$_2$SO$_4$). Evaporation of the solvent and chromatography of the oily residue [silica, ethyl acetate/hexanes (3:7)] afforded a white, crystalline solid (2.18 g, 92%): mp 56-57° C.; IR (film, ν$_{max}$ cm$^{-1}$) 1762, 1752, 1685, 1600; $^1$H NMR δ 1.48 (s, 9H), 4.60 (s, 2H), 6.99 (d, J=8.7 Hz, 2H), 7.84 (d, J=8.7 Hz, 2H), 9.89 (s, 1H); $^{13}$C NMR δ 28.25, 65.76, 83.17, 115.08, 130.82, 132.18, 163.00, 167.37, 190.98; EI-MS 105/107, 135, 193/194, 236/237; FAB-MS obsd 237.1120, calcd 237.1127 [(M+H)$^+$, M=C$_{13}$H$_{16}$O$_4$]; Anal. Calcd C, 66.09; H, 6.83. Found C, 66.06; H, 6.82.

5-[4-(tert-Butoxycarbonylmethoxy)phenyl]dipyrromethane (7a). Following a standard procedure,$^{23}$ aldehyde 6 (2.07 g, 8.78 mmol) was dissolved in dry pyrrole (56 mL, 878 mmol), and the solution was flushed with argon for 10 min. InCl$_3$ (666 mg, 0.80 mmol) was added, and the reaction was allowed to proceed for 3 h. The reaction was quenched by addition of powdered NaOH (977 mg, 24.43 mmol). The mixture was stirred for 45 min. The mixture was filtered. The filtrate was concentrated at reduced pressure. Chromatography [silica, ethyl acetate/CH$_2$Cl$_2$/hexanes (1:2:7)] afforded a pale yellow oil (2.73 g, 88%): IR (film, ν$_{max}$ cm$^{-1}$) 1744, 1608; $^1$H NMR δ 1.49 (s, 9H), 4.49 (s, 2H), 5.42 (s, 1H), 5.90 (app s, 2H), 6.15 (d, J=2.7 Hz, 2H), 6.69 (app s, 2H), 6.83 (d, J=9.0 Hz, 2H) 7.12 (d, J=9.0 Hz, 2H), 7.93 (br, 2H); $^{13}$C NMR δ 28.30, 43.35, 65.96, 82.66, 107.32, 108.61, 114.91, 117.40, 129.70, 132.96, 135.33, 157.13, 168.32; EI-MS 145, 229/230, 295/296, 352; FAB-MS obsd 352.1800, calcd 352.1787 (C$_{21}$H$_{24}$N$_2$O$_3$); Anal. Calcd C, 71.57; H, 6.86; N, 7.94. Found C, 71.00; H, 7.04; N, 7.97.

5-[4-(tert-Butoxycarbonylmethoxy)phenyl]-1,9-diformyldipyrromethane (8a). Following a standard procedure,$^{22}$ a solution of 7 (2.66 g, 7.55 mmol) in DMF (7.53 mL) was cooled to 0° C. under argon, and phosphorous oxychloride (1.48 mL, g, mmol) was added. The mixture was allowed to reach room temperature. Stirring was continued for 1 h. The solution was poured into aqueous sodium hydroxide (80 mL of 10 wt % solution), and was extracted into ethyl acetate (5×80 mL). The organic phases were combined, washed with water and brine, dried (Na$_2$SO$_4$), and concentrated. Chromatography on neutral alumina (CH$_2$Cl$_2$/MeOH, 0.5→1%) gave a pale brown solid (1.36 g, 45%): mp 84-85° C. (dec.); IR (film, ν$_{max}$ cm$^{-1}$) 1754, 1599; $^1$H NMR δ 1.47 (s, 9H), 4.48 (s, 2H), 5.52 (s, 1H), 6.03 (d, J=3.9 Hz, 2H), 6.81-6.85 (m, 4H), 7.15 (d, J=8.4 Hz, 2H), 9.21 (s, 2H), 10.20-10.80 (br, 2H); $^{13}$C NMR δ 28.48, 43.79, 65.94, 82.90, 111.64, 115.23, 12.36, 129.79, 132.90, 141.88, 162.82, 168.13, 179.17; FAB-MS obsd 408.1668, calcd 408.1685 (C$_{23}$H$_{24}$N$_2$O$_5$); Anal. Calcd C, 67.63; H, 5.92; N, 6.86. Found C, 66.43; H, 5.92; N, 6.96.

Dibutyl[5-[4-(tert-Butoxycarbonylmethoxy)phenyl]-1,9-diformyl-5,10-dihydrodipyrrinato]tin(IV) (8aSnBu$_2$). A solution of 8a (1.79 g, 4.39 mmol) in dichloromethane (3.6 mL) was treated with TEA (1.83 mL) and dibutyltin dichloride (1.33 g, 4.38 mmol). The solution was stirred at room temperature for 1 h. The reaction mixture was concentrated at reduced pressure. Chromatography on silica (1% TEA in CH$_2$Cl$_2$) gave a dark orange oil (0.79 g, 28%): IR (film, ν$_{max}$ cm$^{-1}$) 1753, 1599; $^1$H NMR δ 0.70-0.79 (m, 6H), 1.10-1.57 (m, 21H), 4.46 (s, 2H), 5.46 (s, 1H), 6.11 (d, J=3.3 Hz, 2H), 6.79 (d, J=3.3 Hz, 2H), 7.03-7.06 (m, 2H), 9.15 (s, 2H); $^{13}$C NMR δ 13.71, 13.78, 24.14, 24.56, 26.26, 26.50, 27.29, 27.33, 28.27, 66.01, 22.64, 82.60, 115.04, 124.11, 129.42, 136.85, 138.11, 152.52, 157.11, 168.21, 178.79; FAB-MS obsd 641.2004, calcd 641.2037 [(M+H)$^+$, M=C$_{31}$H$_{40}$N$_2$O$_5$Sn]; Anal. Calcd C, 58.23; H, 6.31; N, 4.38. Found C, 58.32; H, 6.36; N, 4.43.

5-[4-(tert-Butoxycarbonylmethoxy)phenyl]-1,9-bis(N-propylimino)dipyrromethane (9a). A solution of 8a (1.49 g, 3.64 mmol) in THF (12 mL) was treated with propylamine (6.0 mL). The solution was stirred at room temperature for 1 h. The volatile components were evaporated, and the sample was dried at reduced pressure, affording a pale brown solid (quantitative): mp 119-121° C.; IR (film, ν$_{max}$ cm$^{-1}$) 1755, 1639; $^1$H NMR δ 0.88 (t, J=7.5 Hz, 6H), 1.48 (s, 9H), 1.55-1.62 (m, 4H), 3.37 (t, J=6.6 Hz, 4H), 4.47 (s, 2H), 5.36 (s, 1H), 5.88 (d, J=3.6 Hz, 2H), 6.32 (d, J=3.6 Hz, 2H), 6.81 (d, J=8.7

Hz, 2H), 7.09 (d, J=8.7 Hz, 2H), 7.88 (s, 2H); $^{13}$C NMR δ 12.04, 24.51, 28.29, 43.76, 62.90, 66.01, 82.58, 109.31, 114.55, 114.96, 129.68, 130.39, 134.24, 136.73, 151.68, 157.21, 168.26, 20.98; FAB-MS obsd 491.3026, calcd. 491.3022 [(M+H)$^+$, M=$C_{29}H_{38}N_4O_3$]; Anal. Calcd C, 70.99; H, 7.81; N, 11.42. Found C, 71.09; H, 7.81; N, 11.38.

Zn(II)-5-[1,5-Bis(tert-butyldimethylsilyloxy)pent-3-yl]-15-[4-(tert-butoxycarbonylmethoxy)phenyl]porphyrin (10a). A solution of 9a (132 mg, 0.269 mmol) and 5 (142 mg, 0.298 mmol) in toluene (30.0 mL) was treated with Zn(OAc)$_2$ (550 mg, 3.00 mmol). The mixture was refluxed for 18 h open to the air. The toluene was evaporated and the residue was chromatographed (silica, CH$_2$Cl$_2$) to give a purple solid (62 mg, 24%): $^1$H NMR δ-0.19 (s, 12H), 0.75 (s, 18H), 1.62 (s, 9H), 3.03-3.12 (m, 2H), 3.25-3.37 (m, 2H), 3.56-3.71 (m, 2H), 4.80 (s, 2H), 5.93 (m, 1H), 7.29-7.33 (m, 2H), 8.12-8.15 (m, 2H), 9.10-9.12 (m, 2H), 9.38-9.40 (m, 2H), 9.46-9.50 (m, 2H), 9.91 (d, J=4.8 Hz, 1H), 10.04 (d, J=5.1 Hz, 1H), 10.25 (s, 2H); LD-MS obsd 908.4; FAB-MS obsd 908.3694, calcd 908.3707 ($C_{49}H_{64}N_4O_5Si_2Zn$); $λ_{abs}$ (log ε) 408 (4.64), 538 nm; $λ_{em}$ ($λ_{exc}$ 408 nm) 580, 634 nm.

Zn(II)-5-(4-tert-Butoxycarbonylmethoxyphenyl)-5-(1,5-dihydroxypent-3-yl)-porphyrin (11a). A solution of 10a (48.7 mg, 0.05 mmol) was dissolved in THF containing TBAF (3.0 mL of 1.0 M solution, water content ~5%). The reaction mixture was cooled in an ice-water bath and the reaction was allowed to proceed for 1 h. Then the mixture was poured into ethyl acetate and the organic phase was washed with water. The aqueous layer was extracted with ethyl acetate. The combined organic phases were washed with water and dried (Na$_2$SO$_4$). The sample was concentrated. Anhydrous zinc acetate (200 mg, 1.1 mmol) was added, and the mixture was stirred at room temperature for 15 min. Column chromatography [neutral alumina, CH$_2$Cl$_2$/MeOH (2→10%)] afforded a bright purple solid (31.8 mg, 78%): $^1$H NMR δ 1.53 (s, 9H), 2.95-2.99 (m, 2H), 3.19-3.24 (m, 2H), 3.48-3.52 (m, 2H), 4.74 (s, 2H), 5.71 (m, 1H), 7.21 (d, J=7.8 Hz, 2H), 8.05 (d, J=7.8 Hz, 2H), 8.95 (s, 2H), 9.24 (s, 2H), 9.32-9.33 (m, 2H), 9.69-9.70 (m, 1H), 9.80-9.81 (m, 1H), 10.06 (s, 2H); LD-MS obsd (−) 678.7, calcd 678.2185 ($C_{38}H_{38}N_4O_4Zn$); $λ_{abs}$ (log ε) 411 (5.22), 540 nm; $λ_{em}$ ($λ_{exc}$ 411 nm) 583, 635 nm.

Zn(II)-5-(4-tert-Butoxycarbonylmethoxyphenyl)-15-[1,5-bis(dimethoxyphosphoryloxy)pent-3-yl]porphyrin (12a). A solution of 9a (211 mg, 0.431 mmol) and 5c (200 mg, 0.431 mmol) in toluene (46 mL) was treated with anhydrous zinc acetate (0.81 g, 4.3 mmol). The mixture was refluxed open to the air for 18 h. The toluene was evaporated. The crude product was dried. Column chromatography [silica, CH$_2$Cl$_2$/EtOAc (0→20%) then CH$_2$Cl$_2$/methanol (0→2%)] afforded a deep red solid (87 mg, 22%): $^1$H NMR δ 2.81-3.00 (m, 12H), 3.19-2.28 (m, 2H), 3.33-3.37 (m, 4H), 4.80 (s, 2H), 5.48-5.55 (m, 1H), 7.28-7.31 (m, 2H), 8.11-8.16 (m, 2H), 9.05-9.06 (m, 2H), 9.27-9.38 (m, 3H), 9.41-9.42 (m, 1H), 9.55-9.61 (m, 2H), 10.08 (s, 1H), 10.16 (s, 1H); LD-MS obsd 896.8; FAB-MS obsd 896.1970, calcd 896.1930 ($C_{41}H_{46}N_4O_{11}P_2Zn$); $λ_{abs}$ (log ε) 412 (4.96), 541 nm; $λ_{em}$ ($λ_{exc}$ 412 nm) 591, 638 nm.

5-[4-(Carboxymethoxy)phenyl]-15-[1,5-bis(dimethoxyphosphoryloxy)pent-3-yl]porphyrin (13a). A solution of 12a (41.9 mg, 0.050 mmol) in CH$_2$Cl$_2$ (1.5 mL) was treated with TFA (1.5 mL). The solution was stirred at room temperature for 3 h. The solvents were evaporated. The dark green residue was dissolved in CH$_2$Cl$_2$. The solution was washed with water. The aqueous phase was extracted with CH$_2$Cl$_2$. The combined organic phases were washed with water. The organic layer was dried (Na$_2$SO$_4$). Evaporation of the solvent afforded a dark green solid (29.6 mg, 76%): $^1$H NMR δ 3.05-3.33 (m, 16H), 3.81-4.03 (m, 4H), 4.71 (s, 2H), 5.76 (m, 1H), 7.38 (d, J=8.7 Hz, 2H), 8.02 (d, J=8.7 Hz, 2H), 8.98-8.99 (m, 2H), 9.31-9.35 (m, 2H), 9.44-9.51 (m, 2H), 9.63-9.65 (m, 2H), 9.81-9.83 (m, 2H), 10.27 (s, 2H); LD-MS 778.6 (M+H)$^+$, 801.7 (M+Na)$^+$, 815.7 (M+K)$^+$; FAB-MS obsd 779.2247, calcd 779.2247 [(M+H)$^+$, M=$C_{37}H_{40}N_4O_{11}P_2$]; $λ_{abs}$ 407, 505 nm; $λ_{em}$ ($λ_{exc}$ 407 nm) 635, 699 nm.

Cu(II)-5-(4-(Carboxymethoxy)phenyl)-15-[1,5-bis(dimethoxyphosphoryloxy)pent-3-yl]porphyrin (Cu13a). A solution of 13a (16 mg, 0.02 mmol) in CHCl$_3$/CH$_3$OH (5.0 mL, 9:1 v/v) was treated with Cu(OAc)$_2$.H$_2$O (42 mg, 0.21 mmol). The solution was stirred at room temperature for 12 h. Then water was added to the reaction mixture. The phases were separated. The aqueous layer was extracted with CH$_2$Cl$_2$. The combined organic phase was washed with water. The organic layer was dried (Na$_2$SO$_4$). Evaporation of the solvent afforded a dark orange solid (17 mg, 98%): $λ_{abs}$ (log ε) 405 (4.47), 530 nm.

5-(4-(Carboxymethoxy)phenyl)-15-[1,5-bis(dihydroxyphosphoryloxy)pent-3-yl]porphyrin (14a). A sample of thoroughly dried 13a (11.8 mg, 0.015 mmol) was dissolved in dry CH$_2$Cl$_2$ (2.0 mL) and then treated with TMS-Br (100 μL, 0.760 mmol). The reaction mixture was stirred at room temperature for 3 h under argon. The solvents were evaporated at reduced pressure. The residue was dissolved in MeOH (3.0 mL). The solution was stirred for 1 h at room temperature. The volatile components were evaporated. The solid residue was dissolved in ~0.2 mL aqueous NaOH (15 wt %), and the sample was diluted to ~3 mL with water. The sample was chromatographed (silica C-18, water/MeOH, 0→50%) to afford a dark red solid (8.2 mg, 76%): $^1$H NMR 6 (D$_2$O) 3.61 (m, 4H), 3.95 (m, 2H), 4.33 (m, 2H), 5.04 (s, 2H), 5.89 (m, 1H), 7.57 (d, J=7.8 Hz, 2H), 7.94-7.97 (m, 2H), 8.91 (m, 2H), 9.28-9.34 (m, 2H), 9.78-9.82 (m, 2H), 10.24-10.33 (m, 4H); ESI-MS obsd (+) 362.1 (M+2H)$^{2+}$, 723.1 (M+H)$^+$, 745.1 (M+Na)$^+$ (−) 721.1 (M−H)$^-$, calcd 722.15 (M, M=$C_{33}H_{32}N_4O_{11}P_2$); $λ_{abs}$ 402, 506 nm; $λ_{em}$ ($λ_{exc}$ 402 nm) 628, 688 nm; HPLC (20% B, 1.5 mL/min, $t_R$=2.22 min).

Cu(II)-5-(4-(Carboxymethoxy)phenyl)-15-[1,5-bis(dihydroxyphosphoryloxy)pent-3-yl]porphyrin (Cu14a). A sample of thoroughly dried Cu13a (28.7 mg, 0.034 mmol) was dissolved in dry CH$_2$Cl$_2$ (1.5 mL) and then treated with TMS-Br (111 μL, 0.84 mmol). The reaction mixture was stirred at room temperature for 3 h under argon. The solvents were evaporated at reduced pressure. The residue was dissolved in MeOH (3.0 mL). The solution was stirred for 1 h at room temperature. The volatile components were evaporated. The sample was chromatographed (silica C-18, water/MeOH, 0→50%) to afford an orange solid (12.2 mg, 12.2%, 46%): ESI-MS obsd 391.0, 782.4, calcd 784.0, 391.5 [(M−2H)$^{2-}$, M=$C_{33}H_{30}N_4O_{11}P_2$], also obsd: 796.2 (M+methylene)$^+$; $λ_{abs}$ 402, 530 nm.

5-(4-(tert-Butoxycarbonylmethoxy)phenyl)-15-(1,5-dibromopent-3-yl)porphyrin (15a). Following a standard method,[29] a solution of 11a (35.6 mg, 57 λmol) in dry CH$_2$Cl$_2$ (12 mL) was treated with CBr$_4$ (53.5 mg, 0.16 mmol). The solution was cooled in an ice-water bath for 10 min. Triphenylphosphine (84 mg, 0.32 mmol) was added. The solution was allowed to warm to room temperature. The reaction was allowed to proceed at room temperature for 12 h. Water was added, and the phases were separated. The aqueous phase was extracted with CH$_2$Cl$_2$. The combined organic phase was washed with water. The organic layer was dried (Na$_2$SO$_4$). Chromatography (silica, CH$_2$Cl$_2$) afforded a dark green solid (38.7 mg, 91%): $^1$H NMR δ −2.86 (s, 1H), −2.82 (s, 1H), 1.64 (s, 9H), 3.24-3.39 (m, 6H), 3.65-3.75 (m, 2H), 4.85 (s, 2H), 5.83 (m, 1H), 7.35 (d, J=8.1 Hz, 2H), 8.18 (d, J=8.1 Hz, 2H), 9.08-9.11 (m, 2H), 9.37-9.60 (m, 5H), 9.98 (d, J=4.2 Hz, 1H), 10.30 (s, 2H); LD-MS obsd 745.1, calcd 742.1154 ($C_{37}H_{36}Br_2N_4O_3$); $\lambda_{abs}$ (log ϵ) 407 (5.00), 503 nm; $\lambda_{em}$ ($\lambda_{exc}$ 407 nm) 635, 701 nm.

5-(4-(tert-Butoxycarbonylmethoxy)phenyl)-15-[1,5-bis(dimethoxyphosphoryl)pent-3-yl]porphyrin (16a). A sample of 15a (38.7 mg, 0.048 mmol) was dissolved in trimethylphosphite (5.0 mL). The solution was refluxed under argon for 1.5 days. The P(OMe)$_3$ was evaporated at reduced pressure. The residue was chromatographed (silica, $CH_2Cl_2$/MeOH, 0→5%) to yield a dark purple solid (24.6 mg, 65%): $^1$H NMR δ 1.64 (s, 9H), 3.15 (m, 2H), 3.32-3.36 (m, 2H), 3.43 (s, 3H), 3.47 (s, 6H), 3.50 (s, 3H), 3.81-3.87 (m, 4H), 4.84 (s, 2H), 5.44 (m, 1H), 7.35 (d, J=8.1 Hz, 2H), 8.17 (d, J=8.1 Hz, 2H), 9.10 (s, 2H), 9.40 (s, 2H), 9.50-9.51 (m, 1H), 9.73-9.74 (m, 2H), 10.30-10.31 (m, 2H); LD-MS obsd 803.7, calcd 800.3104 ($C_{41}H_{48}N_4O_9P_2$); $\lambda_{abs}$ (log ϵ) 407 (4.90), 504 nm; $\lambda_{em}$($\lambda_{exc}$ 407 nm) 636 nm, 702 nm. Varying amounts of a less polar purple solid (16a-Br) were isolated along with small amounts of the starting material 15a (limited characterization). Data for 16a-Br: $^1$H NMR δ 0.86-0.95 (m, 1H), 1.65 (s, 9H), 1.91-2.00 (m, 1H), 3.13-3.40 (m, 6H), 3.44 (s, 3H), 3.48 (s, 3H), 3.55-3.85 (m, 2H), 4.83 (s, 2H), 5.51-5.61 (m, 1H), 7.34 (d, J=8.1 Hz, 2H), 8.17 (d, J=8.1 Hz, 2H), 9.08-9.10 (m, 2H), 9.37-9.41 (m, 2H), 9.49-9.51 (m, 2H), 9.67-9.68 (m, 1H), 9.84-9.85 (m, 1H), 10.30 (s, 2H); LD-MS obsd 773.6, calcd 773.2 [(M+H)$^+$, M=$C_{39}H_{42}BrN_4O_6P_2$]; $\lambda_{abs}$ 407, 502 nm; $\lambda_{em}$ ($\lambda_{exc}$ 407 nm) 634, 702 nm.

5-(4-(Carboxymethoxy)phenyl)-15-[1,5-bis(dihydroxyphosphoryl)pent-3-yl]porphyrin (17a). A solution of 16a (18.8 mg, 0.024 mmol) was dissolved in anhydrous CHCl$_3$ (2 mL). The solution was flushed with Ar for 10 min. Bromotrimethylsilane (400 µL, 3.03 mmol) was added, and the solution was refluxed for 4 h. The reaction mixture was allowed to cool to room temperature. The volatile components were evaporated. The residue was dissolved in MeOH (3 mL). The solution was stirred at room temperature for 1 h. The solvent was evaporated. Aqueous NaOH (0.3 mL, 15 wt %) was added. The mixture was diluted to ~3 mL with distilled water. The sample was purified by reverse phase silica column chromatography (C-18 silica, H$_2$O/MeOH, gradient) to yield a red solid (9.8 mg, 58%): $^1$H NMR (D$_2$O) δ 0.74-0.88 (m, 2H), 1.61-1.75 (m, 2H), 3.00-3.16 (m, 4H), 5.29 (s, 1H), 7.10 (m, 2H), 7.54 (m, 2H), 8.36 (m, 2H), 8.91 (br, 2H), 9.01 (br, 2H), 9.45 (br, 1H), 9.56 (br, 1H), 9.98-10.13 (m, 1H); ESI-MS obsd 691.1 (M+H)$^+$, 346.1 (M+2H)$^{2+}$, 713.2 (M+Na)$^+$, calcd 690.2 ($C_{33}H_{32}N_4O_9P_2$); $\lambda_{abs}$ (H$_2$O) 402, 506 nm; $\lambda_{em}$ ($\lambda_{exc}$ 402 nm) 627, 688 nm; HPLC (2% B, 1.5 mL/min, $t_R$=2.77 min).

Zn(II)-5-(4-(Carboxymethoxy)phenyl)-15-[1,5-bis(dihydroxyphosphoryl)pent-3-yl]porphyrin (Zn17a) (by in situ metalation of 17a). A solution of 16a (10.4 mg, 0.013 mmol) was dissolved in anhydrous CHCl$_3$ (2 mL). The solution was flushed with Ar for 10 min. Bromotrimethylsilane (300 µL, 2.27 mmol) was added, and the solution was refluxed for 4 h. The reaction mixture was allowed to cool to room temperature. The volatile components were evaporated. The residue was dissolved in MeOH (2 mL). The solution was stirred at room temperature for 1 h. The solvent was evaporated. Aqueous NaOH (0.3 mL, 15 wt %) was added. The sample was diluted with distilled water (3 mL). The mixture was treated with Zn(OAc)$_2$ (55 mg, 0.30 mmol) for 1 h. A second portion of aqueous NaOH (0.3 mL, 15 wt %) was added. The sample was purified by reverse phase silica column chromatography (C-18 silica, water/MeOH, 0→50%)] to yield a bright purple solid (9.1 mg, 93%): $^1$H NMR (D$_2$O) δ 1.17-1.30 (m, 2H), 2.01-2.15 (m, 2H), 3.38-3.49 (m, 4H), 5.05 (s, 2H), 5.72 (s, 1H), 7.74 (d, J=6.9 Hz, 2H), 8.37 (d, J=6.9 Hz, 2H), 9.33 (m, 2H), 9.71 (m, 2H), 9.90 (m, 2H), 10.36-10.38 (m, 1H), 10.44-10.46 (m, 1H), 10.57 (s, 1H), 10.60 (s, 1H); ESI-MS obsd 376.9 (M+2H)$^{2+}$, 753.0 (M+H)$^+$, 774.9 (M+Na)$^+$, calcd 752.0779 ($C_{33}H_{30}N_4O_9P_2Zn$); $\lambda_{abs}$ (H$_2$O) 409, 544 nm; $\lambda_{em}$ ($\lambda_{exc}$ 409 nm) 590, 641 nm; HPLC (30% B, 1.5 mL/min, $t_R$=2.38 min).

5-(4-Bromophenyl)dipyrromethane (7b). Following the standard procedure,[23] 4-bromobenzaldehyde (5.55 g, 30.0 mmol) was dissolved in dry pyrrole (208 mL, 3.00 mol), and the solution was flushed with argon for 10 min. InCl$_3$ (666 mg, 3.00 mmol) was added, and the reaction was allowed to proceed for 90 min. The reaction was quenched by addition of powdered NaOH (3.60 g, 90.0 mmol). The mixture was stirred for 45 min. The mixture was filtered. The filtrate was concentrated at reduced pressure. Chromatography [silica, ethyl acetate/CH$_2$Cl$_2$/hexanes (1:2:7)] afforded a pale yellow solid (8.29 g, 92%): mp 120-122° C.; IR (film, $v_{max}$ cm$^{-1}$) 1487; $^1$H NMR δ 5.43 (s, 1H), 5.88-5.89 (m, 2H), 6.15-6.16 (m, 2H), 6.70-6.71 (m, 2H), 7.06-7.08 (m, 2H) 7.42-7.44 (m, 2H), 7.88-7.93 (br, 2H); $^{13}$C NMR δ 43.66, 107.65, 108.80, 112.61, 117.73, 121.08, 130.36, 131.92, 141.40; EI-MS 145, 234/236, 300/302; FAB-MS obsd 300.0257, calcd 300.0262 ($C_{15}H_{13}BrN_2$); Anal. Calcd C, 59.82; H, 4.53; N, 9.30. Found C, 59.99; H, 4.39; N, 9.19.

5-(4-Bromophenyl)-1,9-diformyldipyrromethane (8b). Following a standard procedure,[22] a solution of 5-(4-bromophenyl)dipyrromethane (1.51 g, 5.00 mmol) in DMF (5.00 mL) was cooled to 0° C. under argon, and phosphorous oxychloride (980 µL) was added. The mixture was allowed to reach room temperature. Stirring was continued for 1 h. The solution was poured into aqueous sodium hydroxide (50 mL of 10 wt % solution), and was extracted into ethyl acetate (5×50 mL). The organic phases were combined, washed with water and brine, dried (Na$_2$SO$_4$), and chromatographed [neutral alumina, CH$_2$Cl$_2$/MeOH (0.5→1%)] to afford a pale brown solid (1.43 g, 80%): mp 79-80° C. (dec.); IR (film, $v_{max}$ cm$^{-1}$) 1645, 1485; $^1$H NMR δ 5.54 (s, 1H), 6.03-6.05 (m, 2H), 6.85-6.87 (m, 2H), 7.17 (d, J=7.1 Hz, 2H), 7.46 (d, J=7.1 Hz, 2H), 9.18 (s, 2H), 10.60-10.70 (br, 2H); $^{13}$C NMR δ 44.14, 112.07, 121.89, 122.68, 130.48, 132.27, 132.93, 138.63, 141.61, 179.37; FAB-MS obsd 356.0173, calcd 356.0160 ($C_{17}H_{13}BrN_2O_2$); Anal. Calcd C, 57.16; H, 3.67; N, 7.84. Found C, 56.90; H, 3.64; N, 7.77.

Dibutyl[5-(4-bromophenyl)-1,9-diformyl-5,10-dihydrodipyrrinato]tin(IV) (8bSnBu$_2$). A solution of 8b (1.554 g, 4.35 mmol) in dichloromethane (3.5 mL) was treated with TEA (1.82 mL) and dibutyltin dichloride (1.32 g, 4.34 mmol). The solution was stirred at room temperature for 1 h. The reaction mixture was concentrated at reduced pressure. Chromatography on silica (1% TEA in CH$_2$Cl$_2$) gave a readily crystallizing pink solid (0.41 g, 16%): mp 115-117° C.; IR (film, $v_{max}$ cm$^{-1}$) 1601; $^1$H NMR δ 0.70-0.80 (m, 6H), 1.12-1.59 (m, 6H), 5.49 (s, 1H), 6.13 (d, J=3.9 Hz, 2H), 7.00 (d, J=8.1 Hz, 2H), 7.06 (d, J=3.9 Hz, 2H), 7.39 (d, J=8.1 Hz, 2H), 9.17 (s, 2H); $^{13}$C NMR δ 13.72, 13.79, 24.16, 24.70, 26.25, 27.27, 27.37, 44.83, 112.62, 115.63, 121.09, 124.12, 130.01, 132.05, 138.24, 142.88, 151.45, 179.09; FAB-MS obsd 589.0500, calcd. 589.0513 [(M+H)$^+$, M=$C_{25}H_{29}BrN_2O_2Sn$]; Anal. Calcd C, 51.06; H, 4.97; N, 4.76. Found C, 51.22; H, 5.02; N, 4.74.

5-(4-Bromophenyl)-1,9-bis(N-propylimino)dipyrromethane (9b). A solution of 8b (488 mg, 1.37 mmol) in THF (4.6 mL) was treated with propylamine (2.25 mL, 27.4 mmol). The solution was stirred at room temperature for 1 h. The volatile components were evaporated, and the sample was dried at reduced pressure, affording a pale brown solid:

mp 136-138° C.; IR (film, $v_{max}$ cm$^{-1}$) 1634, 1485; $^1$H NMR δ 0.89 (m, 6H), 1.59 (m, 4H), 3.39 (m, 4H), 5.36 (s, 1H), 5.88 (app s, 2H), 6.34 (app s, 2H), 7.05 (d, J=7.1 Hz, 2H), 7.40 (d, J=7.1 Hz, 2H), 7.90 (s, 2H), 8.80-9.05 (br, 2H); $^{13}$C NMR δ 12.04, 24.53, 44.00, 62.77, 109.44, 114.62, 121.10, 130.35, 130.69, 131.74, 136.07, 140.59, 151.84; FAB-MS obsd 439.1503, calcd 439.1497 [(M+H)$^+$, M=$C_{23}H_{27}BrN_4$]; Anal. Calcd C, 62.87; H, 6.19; N, 12.75. Found C, 62.76; H, 6.19; N, 12.58;

Zn(II)-5-(4-Bromophenyl)-15-[1,5-bis(tert-butyldimethylsilyloxy)pent-3-yl]porphyrin (10b). A solution of 9b (132 mg, 0.269 mmol) and 5a (142 mg, 0.298 mmol) in toluene (30.0 mL) was treated with Zn(OAc)$_2$ (550 mg, 3.00 mmol). The mixture was refluxed for 18 h open to the air. The ethanol was evaporated and the residue was chromatographed (silica, CH$_2$Cl$_2$) to give a purple solid (62 mg, 24%): $^1$H NMR δ −0.07 (s, 12H), 0.96 (s, 18H), 3.13-3.15 (m, 2H), 3.37-3.44 (m, 2H), 3.67-3.81 (m, 4H), 6.03 (m, 1H), 7.82-7.90 (m, 4H), 8.78-8.80 (m, 2H), 9.04-9.10 (m, 2H), 9.39-9.42 (m, 1H), 9.48-9.50 (m, 2H), 9.93-9.97 (m, 2H), 10.05-10.14 (m, 2H); $^{13}$C NMR δ −0.11, 23.45, 23.80, 31.50, 43.96, 50.83, 67.50, 111.18, 111.46, 116.12, 123.12, 127.61, 129.08, 135.31, 136.46, 137.19, 137.34, 141.40, 147.07, 152.87, 154.27, 154.68, 155.94, 155.12, 155.52, 157.57, 174.92; LD-MS obsd 853.7; FAB-MS obsd 856.2232, calcd 856.2182 ($C_{43}H_{53}BrN_4O_2Si_2Zn$); $\lambda_{abs}$ 409, 539 nm; $\lambda_{em}$ ($\lambda_{exc}$ 409 nm) 578, 633 nm.

Zn(II)-5-(4-Bromophenyl)-15-(1,5-dihydroxypent-3-yl) porphyrin (11b). A sample of 10b (54 mg, 0.063 mmol) was dissolved in dry THF (1.26 mL) containing 1.0 M TBAF (1.26 mmol, 10.0 equiv), and the reaction mixture was stirred overnight at room temperature. The THF was evaporated. The residue was dissolved in ethyl acetate. The solution was washed with water. The aqueous layer was extracted with ethyl acetate. The combined organic phases were washed with water and brine. The sample was dried over Na$_2$SO$_4$. The solvent was evaporated. LD-MS indicated demetalation (obsd 563), whereupon the solid was dissolved in CHCl$_3$/MeOH (10, mL, 9:1) and Zn(OAc)$_2$ (195 mg, mmol) was added. The mixture was stirred at room temperature for 1 h. Then the sample was concentrated, and the residue was chromatographed on neutral alumina [CH$_2$Cl$_2$/methanol (2→10%)] affording a bright red solid (34.5 mg, 87%): $^1$H NMR (THF-d$_8$) δ 3.04-3.10 (m, 2H), 3.24-3.28 (m, 2H), 3.28-3.62 (m, 4H), 5.96 (m, 1H), 7.95 (d, J=8.1, 2H), 8.14 (d, J=8.1 Hz, 2H), 8.98-8.99 (m, 2H), 9.37-9.38 (m, 2H), 9.42-9.46 (m, 2H), 9.93 (d, J=4.5 Hz, 1H), 10.05 (d, J=4.5 Hz, 1H), 10.19-10.20 (m, 2H); LD-MS obsd 627.2 (M−H)$^-$; FAB-MS obsd 628.0424, calcd 628.0452 ($C_{31}H_{25}BrN_4O_2Zn$); $\lambda_{abs}$ (CH$_2$Cl$_2$/MeOH, 97.5:2.5) (log ε) 408 (4.89), 538 nm; $\lambda_{em}$ ($\lambda_{exc}$ 408 nm) 589, 643 nm.

Zn(II)-5-(4-Bromophenyl)-15-[1,5-bis(dimethoxyphosphoryloxy)pent-3-yl]porphyrin (12b). Method A: A solution of 11b (30 mg, 0.048 mmol) in dry pyridine (1.0 mL) was cooled in an ice-water bath. Dimethyl chlorophosphate (168 µL, 225 mg, 1.56 mmol) was added, and stirring was continued with cooling for 2 h. The reaction mixture was allowed to reach room temperature. The reaction was allowed to proceed for a further 12 h. The sample was poured into CH$_2$Cl$_2$, and was washed with brine. The aqueous layer was extracted with CH$_2$Cl$_2$. The combined organic phases were washed with brine. The organic layer was dried (Na$_2$SO$_4$). LD-MS analysis of the crude mixture indicated partial demetalation (obsd 782), whereupon the residue was dissolved in CHCl$_3$/MeOH (15 mL, 9:1) and Zn(OAc)$_2$ (230 mg, 1.26 mmol) was added. The mixture was stirred at room temperature for 2 h. Column chromatography [silica, CH$_2$Cl$_2$/methanol (1→2%)] afforded a deep red solid (12.5 mg, 30%): $^1$H NMR δ 2.75 (s, 3H), 2.78 (s, 3H), 2.84 (s, 3H), 2.88 (s, 3H), 3.18 (m, 6H), 2.75-2.88 (m, 2H), 5.42 (m, 1H), 7.90 (d, J=8.1 Hz, 2H), 8.07 (d, J=8.1 Hz, 2H), 9.00-9.02 (m, 2H), 9.26-9.62 (m, 6H), 10.09 (s, 1H), 10.21 (s, 1H); LD-MS obsd 842.5; FAB-MS obsd 844.0444, calcd 844.0405 ($C_{35}H_{35}BrN_4O_8P_2Zn$); $\lambda_{abs}$ (log ε) 411 (4.92), 541 nm; $\lambda_{em}$ ($\lambda_{exc}$ 411 nm) 587, 636 nm.

Method B: A solution of 9b (247 mg, 0.50 mmol) and 5c (247 mg, 0.53 mmol) in toluene (58 mL) were treated with anhydrous zinc acetate (1.03 g, 5.65 mmol). The solution was refluxed open to the air for 18 h. The toluene was evaporated. The sample was dried. Column chromatography (silica, CH$_2$Cl$_2$/methanol, 0→2%) afforded a deep red solid (95.5 mg, 21%) with the same physical properties ($^1$H NMR, LD-MS, $\lambda_{abs}$) as the sample obtained with Method A.

5-(4-Bromophenyl)-15-[1,5-bis(dimethoxyphosphoryloxy)pent-3-yl]porphyrin (13b). A solution of 12b (50.6 mg, 0.06 mmol) in CH$_2$Cl$_2$ (2 mL) was treated with TFA (2 mL). The solution was stirred at room temperature for 30 min. The solvents were evaporated. The dark green residue was dissolved in CH$_2$Cl$_2$. The solution was washed with water. The aqueous phase was extracted with CH$_2$Cl$_2$. The organic phases were combined and washed with water. The organic layer was dried (Na$_2$SO$_4$). Column chromatography [silica, CH$_2$Cl$_2$/MeOH (97:3)] afforded a deep purple solid (46 mg, 98%): $^1$H NMR δ 3.22-3.24 (m, 2H), 3.42-3.51 (m, 2H), 3.90-3.99 (m, 2H), 4.01-4.11 (m, 2H), 5.75-5.92 (m, 1H), 7.94-7.96 (m, 2H), 8.11-8.13 (m, 2H), 9.00-9.05 (m, 2H), 9.38-9.43 (m, 2H), 9.45-9.52 (m, 2H), 9.67-9.68 (m, 1H), 9.84-9.85 (m, 1H), 10.30 (s, 1H), 10.32 (s, 1H); LD-MS obsd (−) 782.8; FAB-MS obsd 782.1257, calcd 782.1270 ($C_{35}H_{37}BrN_4O_8P_2$), $\lambda_{abs}$ 405, 504 nm; $\lambda_{em}$ ($\lambda_{exc}$ 405 nm) 635, 700 nm.

Cu(II)-5-(4-Bromophenyl)-15-[1,5-bis(dimethoxyphosphoryloxy)pent-3-yl]porphyrin (Cu13b). A solution of 13b (16.5 mg, 0.021 mmol) in CHCl$_3$/CH$_3$OH (5 mL, 9:1 v/v) was treated with Cu(OAc)$_2$.H$_2$O (42 mg, 0.21 mmol). The solution was stirred at room temperature for 12 h. The solvents were evaporated and the residue was suspended in a small volume of CH$_2$Cl$_2$. Column chromatography (silica, CH$_2$Cl$_2$/MeOH (95:5)] afforded an orange solid (17.6 mg, 99%): LD-MS obsd 846.7, calcd 843.0509 ($C_{35}H_{35}BrCuN_4O_8P_2$).

5-(4-Bromophenyl)-15-(1,5-bis[dihydroxyphosphoryloxy)pent-3-yl]porphyrin (14b). A sample of thoroughly dried 13b (23 mg, 0.031 mmol) was dissolved in dry CH$_2$Cl$_2$ (1.0 mL) and then treated with TMS-Br (25 µL, 0.19 mmol). The reaction mixture was stirred at room temperature for 3 h under argon. The solvents were evaporated at reduced pressure. The residue was dissolved in MeOH (3.0 mL). The solution was stirred for 1 h at room temperature. The volatile components were evaporated. The sample was chromatographed (silica C-18, water/MeOH, 0→50%) to afford a red solid (9.6 g, 43%): $^1$H NMR δ 3.63-3.68 (m, 4H), 3.67-3.99 (m, 2H), 4.30-4.35 (m, 2H), 5.91-5.96 (m, 1H), 7.40 (d, J=6.3 Hz, 2H), 7.75 (d, J=6.3 Hz, 2H), 8.44-8.51 (m, 2H), 8.99-9.02 (br, 1H), 9.13-9.16 (br, 1H), 9.79-9.87 (m, 2H), 10.15-10.18 (m, 1H), 10.33-10.40 (m, 3H); ESI-MS obsd (+) 726.3 (M+H)$^+$, 748.8 (M+Na)$^+$ (−) 724.9 (M−H)$^-$, calcd 726.1 (M=$C_{31}H_{29}BrN_4O_8P_2$); $\lambda_{abs}$ (H$_2$O) 400, 504 nm; $\lambda_{em}$ ($\lambda_{exc}$ 400 nm) 624, 686 nm; HPLC (40% B, 1.5 mL/min, $t_R$=2.94 min).

Cu(II)-5-(4-Bromophenyl)-15-[1,5-bis(dihydroxyphosphoryloxy)pent-3-yl]porphyrin (Cu14b). A sample of thoroughly dried Cu13b (16.5 mg, 0.019 mmol) was dissolved in dry CH$_2$Cl$_2$ (800 µL) and then treated with TMS-Br (18 µL, 0.136 mmol). The reaction mixture was stirred at room temperature for 3 h under argon. The solvents were evaporated at reduced pressure. The residue was dissolved in MeOH (3.0 mL). The solution was stirred for 1 h at room temperature. The volatile components were evaporated. The sample was chromatographed (silica C-18, water/MeOH, 0→50%) to afford a red solid (10.1 g, 68%): ESI-MS (−) obsd 786.1 (M−H)$^-$, calcd 787.0 ($C_{31}H_{27}BrCuN_4O_8P_2$), also obsd: 800.1 (M+methylene)$^+$, 814.2 (M+2-methylene)$^+$; $\lambda_{abs}$ (H$_2$O) 400, 528 nm.

5-(4-Bromophenyl)-15-(1,5-dibromopent-3-yl)porphyrin (15b). Following a standard method,[29] a solution of 11b (52 mg, 83 µmol) in dry CH$_2$Cl$_2$ (20 mL) was treated with CBr$_4$ (84 mg, 0.25 mmol). The solution was cooled in an ice-water bath for 10 min. Triphenylphosphine (132 mg, 0.50 mmol) was added. The solution was allowed to warm to room temperature. The aqueous phase was extracted with CH$_2$Cl$_2$. The combined organic phase was washed with water. The organic layer was dried (Na$_2$SO$_4$). Chromatography (silica, CH$_2$Cl$_2$) afforded a dark green solid (44.5 mg, 78%): $^1$H NMR δ −2.90 (s, 1H), −2.85 (s, 1H), 3.17-3.39 (m, 6H), 3.65-3.74 (m, 2H), 5.81-5.94 (m, 1H), 7.94 (d, J=8.1 Hz, 2H), 8.11 (d, J=8.1 Hz, 2H), 9.02-9.06 (m, 1H), 9.36-9.42 (m, 1H), 9.45-9.47 (m, 1H), 9.51-9.52 (m, 1H), 9.58-9.60 (m, 1H), 9.99 (d, J=4.8 Hz, 1H), 10.30 (s, 2H); LD-MS 688.1, calcd 689.9629 ($C_{31}H_{25}N_4Br_3$); $\lambda_{abs}$ (log ε) 406 (4.96), 503 nm; $\lambda_{em}$ ($\lambda_{exc}$ 407 nm) 633, 700 nm.

5-(4-Bromophenyl)-15-[1,5-bis(dimethoxyphosphoryl) pent-3-yl]porphyrin (16b). A solution of 15b (33 mg, 0.047 mmol) was dissolved in trimethylphosphite (8.0 mL). The solution was refluxed under argon for 2.5 days. The P(OMe)$_3$ was evaporated. The residue was chromatographed (silica, CH$_2$Cl$_2$/MeOH, 0→5%) to yield a dark purple solid (25.9 mg, 72%): $^1$H NMR δ −2.93 (s, 1H), −2.85 (s, 1H), 3.12-3.50 (m, 16H), 5.44 (s, 1H), 7.95 (d, J=8.1 Hz, 2H), 8.12 (d, J=8.1 Hz, 2H), 9.04-9.05 (m, 2H), 9.41-9.51 (m, 4H), 9.74-9.75 (m, 2H), 10.31-10.33 (m, 2H); LD-MS obsd 749.1 (M−H)$^-$; FAB-MS obsd 751.1454, calcd 751.1450 [(M+H)$^+$, M=$C_{35}H_{37}BrN_4O_6P_2$). Varying amounts of a less polar purple solid (16b-Br) were isolated along with small amounts of the starting material 15b (limited characterization). Data for 16b-Br: $^1$H NMR δ 3.14-3.41 (m, 6H), 3.45 (s, 3H), 3.49 (s, 3H), 3.69-3.80 (m, 2H), 5.63-5.63 (m, 1H), 7.95 (d, J=7.5 Hz, 2H), 8.12 (d, J=7.5 Hz, 2H), 9.04-9.05 (m, 2H), 9.39-9.42 (m, 2H), 9.49-9.52 (m, 2H), 9.69 (d, J=4.2 Hz, 1H), 9.86 (d, J=4.2 Hz, 1H), 10.31-10.32 (m, 2H); LD-MS obsd 718.3, calcd 720.1 ($C_{33}H_{31}Br_2N_4O_3P$); $\lambda_{abs}$ 406, 502 nm; $\lambda_{em}$ ($\lambda_{exc}$ 406 nm) 633, 699 nm.

5-(4-Bromophenyl)-15-[1,5-bis(dihydroxyphosphoryl) pent-3-yl]porphyrin (17b). A solution of 16b (11 mg, 0.015 mmol) in anhydrous CHCl$_3$ (2 mL) under argon was treated with TMS-Br (300 µL, 2.27 mmol). The sample was refluxed for 4 h. The mixture was concentrated and the residue was dissolved in MeOH (3 mL). The mixture was stirred for 1 h. Evaporation of the solvent yielded a dark green solid, which was dissolved in dilute aqueous NaOH. Chromatography (C-18 silica, water/MeOH, gradient) yielded a dark red solid (6.1 mg, 60%): $^1$H NMR δ 0.88-0.97 (m, 2H), 1.70-1.84 (m, 2H), 2.96-3.08 (m, 2H), 3.09-3.24 (m, 2H), 5.21-5.33 (m, 1H), 6.85 (br, 2H), 7.30 (br, 2H), 7.91-7.95 (m, 2H), 8.36 (br, 1H), 8.52 (br, 1H), 9.35 (br, 1H), 9.48 (br, 1H), 9.62 (br, 1H), 9.82 (br, 1H), 9.95 (s, 1H), 10.03 (s, 1H); LD-MS obsd 693.8, ESI-MS obsd 695.0 (M+H)$^+$, 717.0 (M+Na)$^+$, 348.0 (M+2H)$^{2+}$, calcd 694.1 ($C_{31}H_{29}BrN_4O_6P_2$); $\lambda_{abs}$ (H$_2$O) 400, 504 nm; $\lambda_{em}$ ($\lambda_{exc}$ 400 nm) 625, 687 nm; HPLC (40% B, 1.5 mL/min, t$_R$=2.23 min).

Zn(II)-5-(4-Bromophenyl)-15-[1,5-bis(dihydroxyphosphoryl)pent-3-yl]porphyrin (Zn17b)

A solution of 16b (18.9 mg, 0.025 mmol) in anhydrous CHCl$_3$ (2 mL) under argon was treated with TMS-Br (200 µL, 1.51 mmol). The reaction mixture was refluxed for 4 h. The volatile components were evaporated and the residue was dissolved in MeOH (3 mL). The mixture was stirred for 1 h. The mixture was treated with dilute aqueous NaOH (0.2 mL of 15 wt % solution). Zn(OAc)$_2$·2H$_2$O (125 mg, 0.57 mmol) was added, and stirring was continued for 1 h. Evaporation of the methanol, addition of 0.1 mL of aqueous NaOH, followed by 3 mL of water, and purification of the sample by reversed-phase silica column chromatography (C-18 silica, water/MeOH 0→50%) yielded a deep purple solid (7.7 mg, 41%): $^1$H NMR (D$_2$O) δ 0.72 (dd, 2H, J$_1$=13.2 Hz, J$_2$=15.6 Hz, 2H), 1.64 (dd, 2H, J$_1$=14.4 Hz, J$_2$=14.1 Hz, 2H), 2.96 (br, 2H), 5.36 (br, 1H), 7.65 (m, 2H), 8.76 (m, 2H), 9.17 (m, 1H), 9.49 (m, 1H), 9.53 (m, 1H), 10.01 (m, 1H), 10.09 (m, 1H), 10.14 (m, 1H), 10.20 (m, 1H); ESI-MS obsd 755.7 (M+H)$^+$, 380.2 (M+2H)$^{2+}$, calcd 756.0 ($C_{31}H_{27}BrN_4O_6P_2Zn$); $\lambda_{abs}$ 409, 542 nm; $\lambda_{em}$ ($\lambda_{exc}$ 409 nm) 589, 640 nm; HPLC (50% B, 1.5 mL/min, t$_R$=2.25 min).

meso-Tetrakis[1,5-bis(tert-butyldimethylsilyloxy)pent-3-yl]porphyrin (18)

A solution of 4 (360 mg, 1.00 mmol) and pyrrole (70 µL, 1.00 mmol) in CHCl$_3$ (100 mL) was treated with NaCl (1.46 g, 25.0 mmol). The mixture was flushed with Ar for 10 min. The reaction was initiated with BF$_3$·OEt$_2$ (41 µL, 0.33 mmol). Stirring was continued overnight. The solvent was removed at reduced pressure. Column chromatography [silica, hexanes/CH$_2$Cl$_2$ (1:1)] yielded a dark purple solid (41 mg, 10%): $^1$H NMR δ −2.46 (br, 2H), −0.15 (s, 48H), 0.86 (s, 72H), 2.88-2.92 (m, 8H), 3.11-3.16 (m, 8H), 3.61-3.69 (m, 16H), 5.57 (m, 4H), 9.49 (m, 4H), 9.66 (m, 4H); $^{13}$C NMR δ −0.00, 23.72, 31.45, 35.18, 45.22, 50.33 (br), 67.33, 116.15, 174.86; LD-MS 1631.9; FAB-MS obsd 1631.0, calcd 1631.1 ($C_{88}H_{166}N_4O_8Si_8$); $\lambda_{abs}$ 421, 522 nm; $\lambda_{em}$ ($\lambda_{exc}$ 421 nm) 665, 732 nm.

Zn(II)-meso-Tetrakis[1,5-bis(tert-butyldimethylsilyloxy) pent-3-yl]porphyrin (Zn18)

A solution of 18 (20 mg, 0.012 mmol) in CHCl$_3$/MeOH (5 mL, 9:1) was treated with Zn(OAc)$_2$·2H$_2$O (100 mg, 0.46 mmol). The reaction mixture was stirred at room temperature for 2 h. The solvents were evaporated. Chromatography (silica, CH$_2$Cl$_2$) afforded a dark red solid (15.6 mg, 78%): $^1$H NMR δ −0.19 (s, 48H), 0.84 (s, 72H), 2.92-2.98 (m, 8H), 3.17-3.21 (m, 8H), 3.61-3.68 (m, 16H), 5.65 (m, 4H), 9.49 (m, 4H), 9.66-9.68 (m, 4H); LD-MS 1686.9; FAB-MS obsd 1695.0, calcd 1692 ($C_{88}H_{164}N_4O_8Si_8Zn$); $\lambda_{abs}$ 422, 556 nm; $\lambda_{em}$ ($\lambda_{exc}$ 422 nm) 606, 657 nm.

REFERENCES (1) (a) Mauzerall, D. *J. Am. Chem. Soc.* 1962, 84, 2437-2445. (b) Mauzerall; D. *J. Phys. Chem.* 1962, 66, 2531-2533. (c) Mauzerall, D. *Biochemistry* 1965, 4, 1801-1810. (d) Carapellucci, P. A.; Mauzerall, D. *Ann. New York Acad. Sci.* 1975, 244, 214-238. (e) Feitelson, J.; Mauzerall, D. *J. Phys. Chem. B* 2002, 106, 9674-9678.

(2) Hambright, P. In *The Porphyrin Handbook*; Kadish, K. M.; Smith, K. M.; Guilard, R., Eds.; Academic Press: San Diego, Calif. 2000, Vol. 3, pp 129-210.
(3) Grahn, M. F.; Giger, A.; McGuinness, A.; de Jode, M. L.; Stewart, J. C. M.; Ris, H-B.; Alternatt, H. J.; Williams, N. S. *Lasers Med. Sci.* 1999, 14, 40-46.
(4) Hornung, R.; Fehr, M. K.; Walt, H.; Wyss, P.; Berns, M. W.; Tadir, Y. *Photochem. Photobiol.* 2000, 72, 696-700.
(5) Zingg, A.; Felber, B.; Gramlich, V.; Fu, L.; Collman, J. P.; Diederich, F. *Helv. Chim. Acta* 2002, 85, 333-351.
(6) Schell, C.; Hombrecher, H. K. *Bioorg. Med. Chem.*, 1999, 7, 1857-1865.
(7) Lamarche, F. et al., *J. Porphyrins Phthalocyanines* 2002, 6, 130-134.
(8) Subbarayan, M. et al., *Biochem. Biophys. Res. Commun.* 2001, 281, 32-36.
(9) Král, V. et al., *J. Med. Chem.* 2002, 45, 1073-1078.
(10) (a) Bisland, S. K. et al., *Bioconjugate Chem.* 1999, 10, 982-992. (b) de Luca, S. et al., *J. Peptide Sci.* 2001, 7, 386-394. (c) Chaloin, L, et al., *Bioconjugate Chem.* 2001, 12, 691-700.
(11) James, D. A. et al., *Bioorg. Med. Chem. Lett.* 1999, 9, 2379-2384.
(12) Karagianis, G.; Reiss, J. A. *Aust. J. Chem.* 1995, 48, 1693-1705.
(13) (a) Bedel-Cloutour, C. H. et al., *J. Immunol. Methods* 1991, 144, 35-41. (b) Bhalgat, M. K. et al., *Nucl. Med. Biol,* 1997, 24, 179-185. (c) Birchler, M et al., *Nat. Biotechnol.* 1999, 17, 984-988. (d) Vrouenraets, M. B. et al., *Int. J. Cancer* 2000, 88, 108-114. (e) Oseroff, A. R. et al., *Photochem. Photobiol.* 1987, 46, 83-96.
(14) Cavanaugh, P. G. *Breast Cancer Res. Treat.* 2002, 72, 117-130.
(15) (a) Gijsens, A.; De Witte, P. *Int. J. Oncol.* 1998, 13, 1171-1177. (b) Gijsens, A. et al., *Cancer Res.* 2000, 60, 2197-2202.
(16) Schmidt-Erfurth, U. et al., *Br. J. Cancer* 1997, 75, 54-61.
(17) Frau, S. et al., *Bioconjugate Chem.* 1997, 8, 222-231.
(18) (a) Soukos, N. S. et al., *Photochem. Photobiol.* 1997, 65, 723-729.
(19) Thamyongkit, P. et al., *J. Org. Chem.* 2004, 69, 3700-3710.
(20) Langhals, H. et al., *Tetrahedron* 2000, 56, 5435-5441.
(21) Fan, D. et al., *Tetrahedron* 2005, 61, 10291-10302.
(22) Taniguchi et al., *J. Porphyrins Phthalocyanines* 2005, 9, 554-574.
(23) Laha, J. K. et al., *Org. Process Res. Dev.* 2003, 7, 799-812.
(24) Vader, J. et al., *Tetrahedron* 1989, 45, 2131-2142.
(25) Tamaru, S.-i. et al., *J. Org. Chem.* 2004, 69, 765-777.
(26) (a) Zhang, D.; Poulter, C. D. *J. Am. Chem. Soc.* 1993, 115, 1270-1277. (b) Xu, Y.; Prestwich, G. D. *J. Org. Chem.,* 2002, 67, 7158-7161.
(27) (a) Muthukumaran, K. et al., *J. Org. Chem.,* 2004, 69, 1444-1452. (b) Loewe, R. S. et al., *J. Org. Chem.* 2004, 69, 1453-1460.
(28) Feng, G. et al., *J. Am. Chem. Soc.* 2005, 127, 13470-13471.
(29) Wedel, M. et al., *Eur. J. Org. Chem.* 2001, 1681-1687.
(30) Marshall, J. A. et al., *J. Org. Chem.* 1987, 52, 2378-2388.

The foregoing is illustrative of the present invention, and is not to be construed as limiting thereof. The invention is defined by the following claims, with equivalents of the claims to be included therein.

That which is claimed is:
1. A chlorin of Formula Va or bacteriochlorin of Formula Vb:

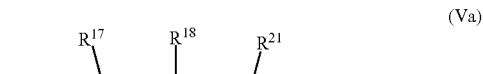

(Va)

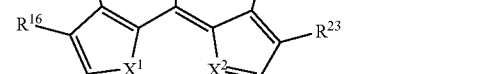

(Vb)

wherein:
M is a metal or is absent;
$X^1$, $X^2$, $X^3$ and $X^4$ are each independently selected from the group consisting of Se, NH, $CH_2$, O and S;
at least one pair of $R^{11}$ and $R^{12}$, $R^{13}$ and $R^{14}$, $R^{21}$ and $R^{22}$, and $R^{23}$ and $R^{24}$ are both independently selected Alk'R', wherein Alk' is a C 1-C50 alkylidene chain, and R' is an ionic group, polar group, bioconjugatable group, or targeting group;
$R^{11}$, $R^{12}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, and groups of Formula II:

(II)

wherein $R^4$ and $R^5$ are each independently an ionic group or polar group, and $Alk^3$ and $Alk^4$ are each independently a C1-C50 alkylidene chain;

wherein each of $R^{11}$ and $R^{12}$, $R^{13}$ and $R^{14}$, $R^{21}$ and $R^{22}$, or $R^{23}$ and $R^{24}$ can together form=O;

and wherein each of $R^{11}$ and $R^{12}$, $R^{13}$ and $R^{14}$, $R^{21}$ and $R^{22}$, or $R^{23}$ and $R^{24}$, can together form spiroalkyl;

or $R^{23}$ is $Alk^{41}R^{41}$ wherein $Alk^{41}$ is a C1-C50 alkylidene chain, and $R^{41}$ is an ionic group, polar group, bioconjugatable group, or targeting group;

or $R^{24}$ is $Alk^{42}R^{42}$ wherein $Alk^{42}$ is a C1-C50 alkylidene chain, and $R^{42}$ is an ionic group, polar group, bioconjugatable group or targeting group;

or a salt thereof.

2. The compound of claim 1, subject to the proviso that $R^{21}$ and $R^{22}$, or $R^{23}$ and $R^{24}$ are not both H when said compound is a bacteriochlorin of Formula Vb.

3. The compound of claim 1, wherein M is present and is selected from the group consisting of Pd, Pt, Mg, Zn, Al, Ga, In, Sn, Cu, Ni, and Au.

4. A compound of claim 1, wherein said compound is a bacteriochlorin of Formula Vb:

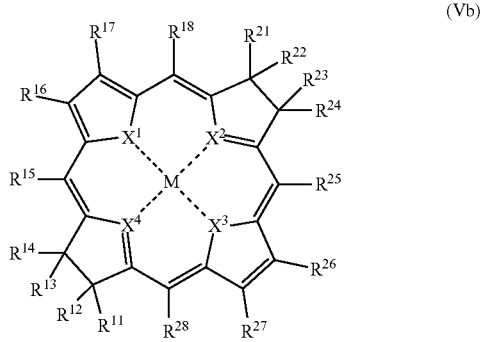

(Vb)

5. The compound of claim 4, wherein:
M is absent;
$X^1$, $X^2$, $X^3$ and $X^4$ are NH;
$R^{11}$ and $R^{12}$ are both independently selected Alk'R', wherein Alk' is a C1-C50 alkylidene chain, and R is an ionic group, polar group, bioconjugatable group, or targeting group;
$R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, and groups of Formula II:

(II)

wherein $R^4$ and $R^5$ are each independently an ionic group or polar group, and $Alk^3$ and $Alk^4$ are each independently a C1-C50 alkylidene chain;

or a salt thereof.

6. The compound of claim 4, wherein:
M is absent;
$X^1$, $X^2$, $X^3$ and $X^4$ are NH;
$R^{11}$ and $R^{12}$ are both independently selected Alk'R', wherein Alk' is a C1-C50 alkylidene chain, and R' is an ionic group, polar group, bioconjugatable group, or targeting group;
$R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each H.

7. The compound of claim 6, wherein Alk' is a C50 alkylidene chain and R' is an polar group.

8. The compound of claim 7, wherein said polar group is amino.

9. A composition comprising:
(a) an aqueous solvent; and
(b) from 1 microMolar to 500 milliMolar of a compound of claim 1 solubilized in said aqueous solvent.

10. A pharmaceutical formulation comprising:
(a) a pharmaceutically acceptable carrier; and
(b) a compound of claim 1 in said carrier.

11. The pharmaceutical formulation of claim 10, wherein said carrier comprises an aqueous carrier, and wherein from 1 microMolar to 500 milliMolar of said compound is solubilized in said aqueous carrier.

12. A composition of claim 11, wherein:
said composition has a peak molar absorption coefficient in solution of 10,000 to 300,000 $M^{-1}cm^{-1}$ at a wavelength between 650 and 900 nanometers; and
said composition has a loss of not more than 20 percent of said compound when stored in a sealed vessel at room temperature in the absence of ambient light for at least 3 months.

13. A composition consisting of a compound of claim 1, wherein:
said composition has a peak molar absorption coefficient in solution of 10,000 to 300,000 $M^{-1}cm^{-1}$ at a wavelength between 650 and 900 nanometers; and
said composition has a loss of not more than 20 percent of said compound when stored in a sealed vessel at room temperature in the absence of ambient light for at least 3 months.

14. A composition comprising a compound of claim 1 in a solvent, wherein
said composition has a peak molar absorption coefficient in solution of 10,000 to 300,000 $M^{-1}cm^{-1}$ at a wavelength between 650 and 900 nanometers; and
said composition has a loss of not more than 20 percent of said compound when stored in a sealed vessel at room temperature in the absence of ambient light for at least 3 months.

15. A composition of claim 14, wherein said solvent comprises an aqueous solvent, and said compound of claim 1 is solubilized in said aqueous solvent in an amount between 1 microMolar and 500 milliMolar.

* * * * *

UNITED STATES PATENT AND TRADEMARK OFFICE
CERTIFICATE OF CORRECTION

PATENT NO.         : 8,530,459 B2
APPLICATION NO.    : 13/316009
DATED              : September 10, 2013
INVENTOR(S)        : Borbas et al.

Page 1 of 1

It is certified that error appears in the above-identified patent and that said Letters Patent is hereby corrected as shown below:

On Title Page:
Item 63, Related U.S. Application Data:
Please correct "PCT/US2006/041040 on Oct. 19, 2009, now"
      to read -- PCT/US2006/041040 on Oct. 19, 2006, now --

In the Specifications:
Column 3, Formula (Va), Lines 55-67:
Please correct the Formula below:

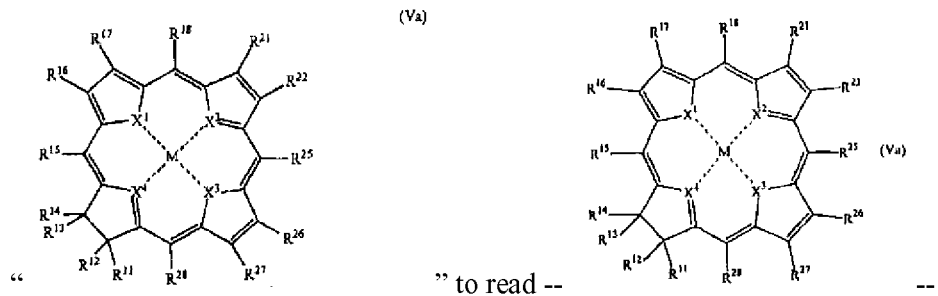

Column 66, Line 31: Please correct "$^1$H NMR 6 (D$_2$O)"
      to read -- $^1$H NMR δ (D$_2$O) --

In the Claims:
Column 75, Claim 5, Line 40: Please correct "chain, and R is an"
      to read -- chain, and R' is an --

Signed and Sealed this
Twenty-second Day of April, 2014

Michelle K. Lee
*Deputy Director of the United States Patent and Trademark Office*